(12) United States Patent
Klymchenko et al.

(10) Patent No.: US 11,697,838 B2
(45) Date of Patent: Jul. 11, 2023

(54) OLIGONUCLEOTIDE-FUNCTIONALIZED HYDROPHOBIC POLYMER NANOPARTICLES

(71) Applicants: UNIVERSITE DE STRASBOURG, Strasbourg (FR); CENTRE NATIONAL DE LA RECHERCHE SCIENTIFIQUE, Paris (FR)

(72) Inventors: Andrii Klymchenko, Illkirch (FR); Nina Melnychuk, Illkirch (FR); Andréas Reisch, Colmar (FR)

(*) Notice: Subject to any disclaimer, the term of this patent is extended or adjusted under 35 U.S.C. 154(b) by 186 days.

(21) Appl. No.: 16/979,309

(22) PCT Filed: Mar. 8, 2019

(86) PCT No.: PCT/EP2019/055847
§ 371 (c)(1),
(2) Date: Sep. 9, 2020

(87) PCT Pub. No.: WO2019/170860
PCT Pub. Date: Sep. 12, 2019

(65) Prior Publication Data
US 2021/0130875 A1    May 6, 2021

(30) Foreign Application Priority Data
Mar. 9, 2018 (EP) ..................................... 18305253

(51) Int. Cl.
*C12Q 1/68* (2018.01)
*C12Q 1/6818* (2018.01)
*B82Y 5/00* (2011.01)

(52) U.S. Cl.
CPC .............. *C12Q 1/6818* (2013.01); *B82Y 5/00* (2013.01); *C12Q 2525/197* (2013.01); *C12Q 2537/161* (2013.01); *C12Q 2563/107* (2013.01); *C12Q 2563/155* (2013.01)

(58) Field of Classification Search
CPC ............ C12Q 1/6818; C12Q 2525/197; C12Q 2537/161; C12Q 2563/107; C12Q 2563/155; B82Y 5/00
See application file for complete search history.

(56) References Cited

PUBLICATIONS

International application No. PCT/EP2019/055847 International Preliminary Report on Patentability Chapter I dated Sep. 15, 2020.
International application No. PCT/EP2019/055847 International Search Report dated Apr. 8, 2019.
International application No. PCT/EP2019/055847 Search Strategy dated Apr. 8, 2019.
International application No. PCT/EP2019/055847 Written Opinion of the International Searching Authority dated Apr. 8, 2019.
European application No. 18305253.9 extended European search report dated Jul. 20, 2018.

(Continued)

*Primary Examiner* — Jezia Riley

(57) ABSTRACT

The present invention concerns an oligonucleotide-functionalized hydrophobic polymer nanoparticle and method of its preparation. Said nanoparticle is a dye-loaded polymeric nanoparticle, and being functionalized by:
(a) target-specific oligonucleotides, and/or
(b) non-specific oligonucleotides.

4 Claims, 11 Drawing Sheets

(56) References Cited

PUBLICATIONS

Figure 1:
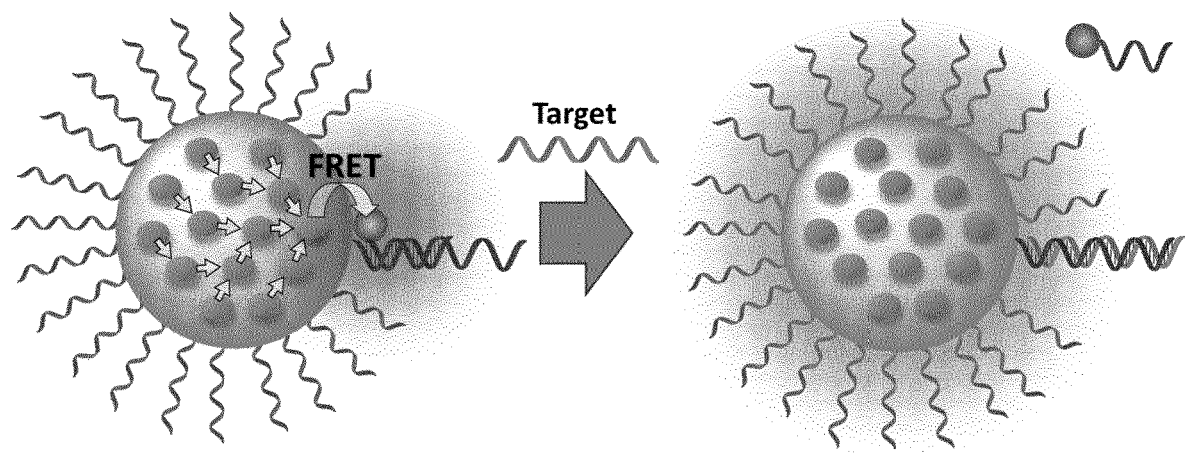

Andreas Reisch et al. "Charge-Controlled Nanoprecipitation as a Modular Approach to Ultrasmall Polymer Nanocarriersz Making Bright and Stable Nanoparticles", ACS NANO, vol. 9, No. 5, Apr. 20, 2015 (Apr. 20, 2015), pp. 5104-5116, XP055573800, US ISSN: 1936-0851, D0I: 10.1021/acsnano.5b00214.

Sarah E. Ochmann et al. "Optical Nanoantenna for Single Molecule-Based Detection of Zika Virus Nucleic Acids without Molecular Multiplication", Analytical Chemistry, vol. 89, No. 23, Dec. 5, 2017 (Dec. 5, 2017), pp. 13000-13007, XP055488875, US ISSN: 0003-2700, DOI: 10.1021/acs.analchem.7b04082.

Nina Melnychuk et al. "DNA-Functionalized Dye-Loaded Polymeric Nanoparticles: Ultrabright FRET Platform for Amplified Detection of Nucleic Acids", Journal of the American Chemical Society, vol. 140, No. 34, Aug. 1, 2018 (Aug. 1, 2018), pp. 10856-10865, XP055573515, ISSN: 0002-7863, DOI: 10.1021/jacs.8b05840.

Alyssa B. Chinen et al. "Nanoparticle Probes for the Detection of Cancer Biomarkers, Cells, and Tissues by Fluorescence", Journal Chemical Reviews, vol. 115, Issue No. 19, State Published: Jan. 1, 2015, Pages (from-to) 10530-10574.

Chun-Yang Zhang et al. "Single-quantum-dot-based DNA nanosensor", Journal Nature Materials, vol. 4, Issue No. 11, State Published—Nov. 2005, Pages (from-to) 826-831.

Jakob G. Woller et al. "Self-Assembled Nanoscale DNA-Porphyrin Complex for Artificial Light Harvesting", Jan. 2013, Journal of the American Chemical Society, 135(7), DOI: 10.1021/ja311828v.

M Monsur Ali et al. "Rolling circle amplification: a versatile tool for chemical biology, materials science and medicine", Chem Soc Rev. May 21, 2014;43(10):3324-41. doi: 10.1039/c3cs60439j.

Shu Wang et al. "Fluorescein Provides a Resonance Gate for FRET from Conjugated Polymers to DNA Intercalated Dyes", J. Am. Chem. Soc. 2004, 126, 17, 5446-5451, Publication Date: Apr. 3, 2004, https://doi.org/10.1021/ia035550m.

Robert M. Dirks et al: "Triggered amplification by hybridization chain reaction", PNAS Oct. 26, 2004 101 (43) 15275-15278; https://doi.org/10.1073/pnas.0407024101; Communicated by Stephen L. Mayo, California Institute of Technology, Pasadena, CA, Sep. 24, 2004 (received for review Jul. 2, 2004).

Omid C. Farokhzad et al. "Targeted nanoparticle-aptamer bioconjugates for cancer chemotherapy in vivo", Omid C. Farokhzad, Jianjun Cheng, Benjamin A. Teply, Ines Sherifi, Sangyong Jon, Philip W. Kantoff, Jerome P. Richie, and Robert Langer; PNAS Apr. 18, 2006 103 (16) 6315-6320; https://doi.org/10.1073/pnas.0601755103; Contributed by Robert Langer, Mar. 3, 2006.

Resham J. Banga, et al. "Drug-loaded Polymeric Spherical Nucleic Acids: Enhancing Colloidal Stability and Cellular Uptake of Polymeric Nanoparticles through DNA Surface-functionalization", Biomacromolecules. Author manuscript; available in PMC Feb. 13, 2018. Published in final edited form as: Biomacromolecules. Feb. 13, 2017; 18(2): 483-489. Published online Jan. 18, 2017. doi: 10.1021/acs.biomac.6b01563.

Tania Nolan et al. "Quantification of mRNA using real-time RT-PCR", Feb. 2006Nature Protocol 1(3):1559-82, DOI: 10.1038/nprot. 2006.236.

Andrew E. Prigodich, et al. "Multiplexed Nanoflares: mRNA Detection in Live Cells", Published in final edited form as: Anal Chem. Feb. 21, 2012; 84(4): 2062-2066. Published online Jan. 30, 2012. doi: 10.1021/ac202648w.

Andreas Reisch et al. "Fluorescent Polymer Nanoparticles Based on Dyes: Seeking Brighter Tools for Bioimaging", Small, First published: Feb. 22, 2016 https://doi.org/10.1002/smll.201503396.

Kateryna Trofymchuk et al. "Giant light-harvesting nanoantenna for signle-molecule detection in ambient light", Nature Photonics 11(10), Oct. 2017, DOI: 10.1038/s41566-017-0001-7.

Wu et al. "Conjugated-Polymer-Amplified Sensing, Imaging, and Therapy", Chem, vol. 2, Issue 6, p. 760-790, Jun. 8, 2017. DOI:https://doi.org/10.1016/j.chempr.2017.05.002.

Lei He et al. "Fluorescence Resonance Energy Transfer-Based DNA Tetrahedron Nanotweezer for Highly Reliable Detection of Tumor-Related mRNA in Living Cells", ACS Nano 2017, 11, 4, 4060-4066 Publication Date:Mar. 22, 2017, https://doi.org/10.1021/acsnano.7b00725.

BSA-Biotin   Neutravidin   DNA-Biotin

Figure 9d
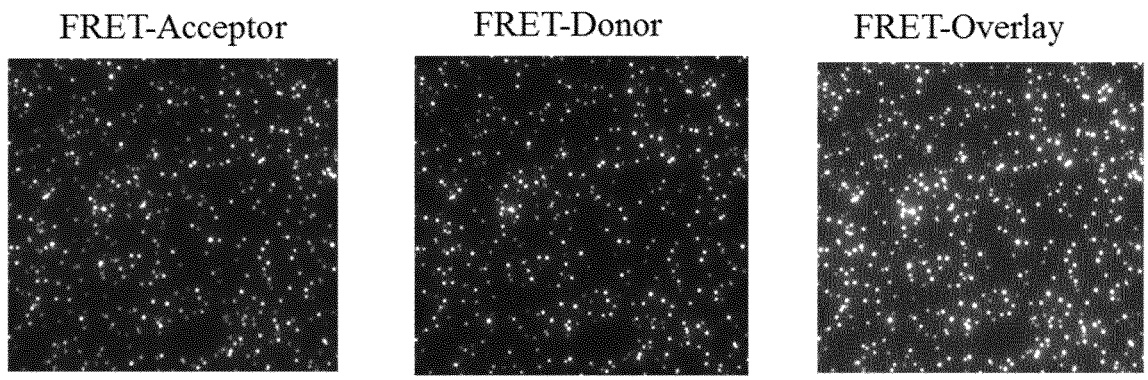
Figure 9e
Figure 9f
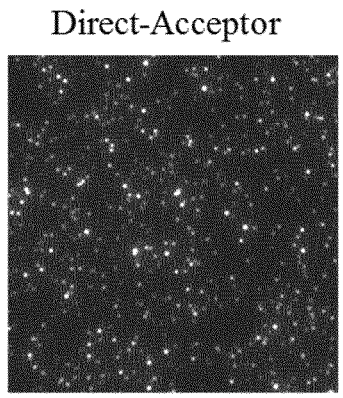
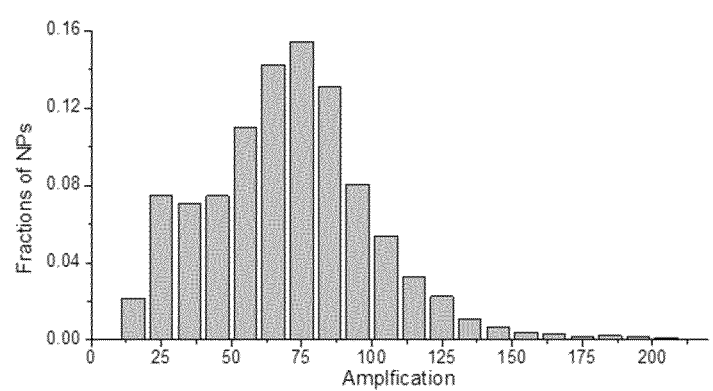

OLIGONUCLEOTIDE-FUNCTIONALIZED HYDROPHOBIC POLYMER NANOPARTICLES

The present invention concerns oligonucleotide-functionalized hydrophobic polymer nanoparticles, their method of production and their use as biosensor.

Ubiquitous nature of nucleic acids makes them universal targets in practically any type of biological research. Detection of nucleic acid, especially messenger RNA (mRNA) and micro-RNA (miRNA) in biological fluids and inside the cells is currently the core in the diagnostics of diseases, such as cancer, viral infections, etc. Therefore, the field of nucleic acid detection has been growing exponentially in recent years. The most sensitive methods for direct detection of nucleic acids in solutions using fluorescent dyes reach limits of detection of around 5 nM. Even the most advanced recent examples of molecular probes using DNA-nanostructures with FRET mechanism enables LOD of 0.33 nM.[1] However, this is often not enough for detecting ultra-low concentrations of nucleic acids in biological samples. Therefore, RNA and DNA detection requires molecular multiplication techniques, notably PCR.[2] However, PCR is a multi-step process that requires complex mixture of expensive reagents, sophisticated equipment and well-trained staff. Moreover, the exponential nature of the amplification using in PCR makes it highly sensitive to contaminations and small variations in the preparation, which can produce false positive and false-negative results. Chemists developed variety of fluorescent probes that can access much lower concentrations of RNA, up to few pM, but they all use molecular multiplication, based on enzymes[3] or hybridization chain reactions.[4]

In earlier works, cationic conjugated polymers were proposed[5], which were used as light-harvesting antenna that could amplify the emission of fluorescent molecules. As the cationic conjugated polymers could strongly bind hybridized sequences, detection limits of specific sequence can be down to the 10 pM range. However, the limitation of cationic conjugated polymers is that they can non-specially interact by ionic forces with other nucleic acids and proteins and their operation depends strongly on the ionic strength.[6]

New possibilities appeared with the development of nanoparticle probes.[7] Thus, nanosensors based on quantum dots were developed, where detection sensitivity was improved (~100-fold) compared to molecular systems by confining multiple (~50) nucleic acid targets around the particle that served as Forster resonance energy transfer (FRET) donor.[8] Mirkin et al proposed to use gold nanoparticles as quencher in the nano-flares approach.[9] Very recently, Tinnefeld et al pioneered plasmonic-based amplification in nucleic acid detection using gold NPs as nanoantenna.[10] This approach requires precise positioning of a fluorophore with respect to gold NPs, which is realized using a sophisticated approach of DNA origami. The amplification achieved was 7.3 on average, although higher values were observed for some NPs.

Dye-loaded polymer NPs, which is rapidly expanding class of organic NPs[11], can also serve as nano-antenna that can amplify the emission of dye thought FRET mechanism. Recently, it has been reported a light-harvesting principle, where >10,000 dyes inside a poly(methyl methacrylate-co-methacrylic acid) (PMMA-MA) NPs transfer efficiently the energy to few acceptors inside NPs. The latter leads to signal amplification (antenna effect) >1000-fold, that in fact surpasses the best plasmonics-based amplification values[12]. In order to convert this giant light-harvesting nanoantenna into DNA nanoprobe, NPs composed of the hydrophobic PMMA-MA polymer should be modified with nucleic acids. However, covalent attachment of hydrophilic molecules, such as an oligonucleotide, to hydrophobic polymers is still a challenge because of different solubility of both components. Therefore, it is difficult (if not impossible) to make a reaction between these two macromolecules, when one of them is not soluble. Surface modification of nanoparticles allows to perform the reaction in buffer and create a hybrid material consisted of oligonucleotide and polymer nanoparticle. However, in this case, there is still the challenge that is to generate small hydrophobic polymer nanoparticles exposing the reactive groups.

Polymer nanoparticles of ~65 nm bearing nucleic acids have been recently developed by Chad Mirkin group using specially designed polymer[13]. In this case, NPs are formed by a copolymer containing a hydrophobic bloc and a hydrophilic bloc, wherein the hydrophilic bloc contains multiple copies of a carboxyl group linked to the main chain of the copolymer by a PEG chain. Nucleotides are coupled with NPs by forming peptide bond with carboxyl group on the surface of NPs. In other existing example relating to NPs of PLGA polymer, a large PEG chain is also coupled to the polymer with terminal carboxyl group[14]. Again, in this case DNA is coupled to the particle through a peptide bond through a PEG linker and the particle size was relatively large (>100 nm).

However, the presence of PEG chain in NPs increases the distances between the nanoparticle and nucleic acids, which may not be compatible with a FRET system, because it requires <5 nm distance between the energy donor and the energy acceptor. In case PEG groups are short or absent, it is known to be necessary to preserve charged (e.g. carboxyl) groups on NPs surface for preventing nanoparticle aggregation.

The method described by Chad Mirkin's group requires the modification of monomer to be able to introduce into a polymer by polymerization a large number of carboxyl groups, which ensures that enough free carboxyl groups remain on nanoparticle surface even though the conjugation with oligonucleotides is also carried out on carboxyl groups of the polymer. This method would not work in case of most common polymers, such as poly(methyl methacrylate-co-methacrylic acid) (PMMA-MA), poly(lactide co-glycolide) (PLGA) and polycaprolactone (PCL), because each polymeric chain of these polymers usually contains only ~1% of monomers with carboxyl group. The poor carboxyl group content in classical hydrophobic polymers greatly decreases the reactivity of these polymers with DNA/RNA and makes it practically impossible to functionalize them with oligonucleotides. Moreover, the method above requires so called "salt-aging process" that uses high salt concentration (300 mM NaCl), which can also be detrimental for nanoparticle stability, especially those containing few charged and/or PEG groups per polymer chain. It is also observed that, preparation of polymer NPs by nanoprecipitation requires charged groups, such as carboxyl groups, on the polymer, which also ensure stability of nanoparticles[15]. However, functionalization of these polymers through carboxylate groups with other reactive groups (e.g. azide for cycloaddition "click" reactions) would lead to polymers without charged groups, which makes impossible preparation of small nanoparticles by nano-precipitation[15].

Taken into account the shortcomings of the above analysed methods for coupling a nucleic acid with a hydrophobic polymeric nanoparticle, it is still necessary to provide new oligonucleotide-functionalized hydrophobic polymer nanoparticles on the one hand having optimal size for efficient FRET fluorescence emission and, on the other hand, being stable in water solution and to develop an easier and more efficient method for coupling nucleic acids with a classical, commercially available hydrophobic polymeric nanoparticles.

The inventors of the present invention solve the problem by an approach of grafting a linker compound bearing both a negative charged group and a reactive group to a hydrophobic polymer. Functional groups are required to be present on the surface of the nanoparticles for covalent attachment of hydrophilic molecules. Against all odds, it is surprising to observe that said linker compound not only introduces into the polymer negative charged groups that will favour formation of small nanoparticles, but also exposes the reactive groups on the nanoparticles surface for further functionalization with nucleic acids.

In fact, the inventors have developed a very simple linker compound bearing at the same time a primary or secondary amine group, a negative group, such as a carboxyl group, and an azide group. By means of its primary amine group, said linker compound reacts with carboxyl groups carried by a classical hydrophobic polymer, such as polyacrylates (e.g. PMMA-MA), polyesters (e.g. PLGA or PCL) and polystyrene derivatives, to introduce into said polymer a motif of formula I', in particular a motif of formula (I), (below) bearing a negative charge group and an azide group:

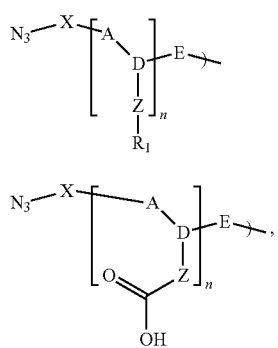

Formula (I')

Formula (I)

wherein:

A represents a spacer chosen from: —(CH$_2$)$_m$—, —(CH$_2$)$_p$NH—CO(CH$_2$)$_q$—, —(CH$_2$)$_p$CO—NH(CH$_2$)$_q$—, —(CH$_2$)$_p$O(CH$_2$)$_q$—, —(CH$_2$)$_p$NH(CH$_2$)$_q$O—, —(CH$_2$)$_m$CO—, —CO(CH$_2$)$_m$—, each of m, p and q represent independently from each other an integer chosen from 0 to 8, preferably an integer chosen from 0 to 5, more preferably an integer chosen from 0 to 3, D represents a group chosen from:

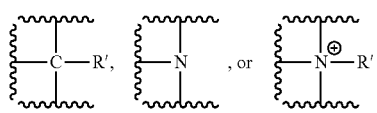

wherein R' represents a hydrogen, a halogen, a (C1-C8)alkyl, a cyclo(C3-C7)alkyl eventually monosubstituted, a monocyclic non-aromatic heterocyclic group eventually monosubstituted, or a monocyclic aromatic group eventually monosubstituted, E represents —(Y—NR$_a$)—, where R$_a$ is H or a (C1-C8) alkyl, X, Y, Z are identical or different and each represent independently of the other a spacer chosen from —(CH$_2$)$_r$—, —(CH$_2$—CH$_2$—O)$_r$—, —(CH$_2$—CH$_2$—NH)$_r$—, —(CH$_2$)$_s$NH—CO(CH$_2$)$_t$—, —(CH$_2$)$_s$CO—NH(CH$_2$)$_t$—, wherein r, s, t represent independently from each other an integer chosen from 0 to 8, preferably an integer chosen from 0 to 5, more preferably an integer chosen from 0 to 3, n represents an integer chosen from 1 to 10, in particular 1 to 3, R$_1$ represents
—COOH,
—PO(OH)$_2$, —PO(OR$_b$)OH, —O—PO(OH)$_2$, —O—PO(OR$_b$)OH, where R$_b$ is methyl or ethyl,
—S(=O)$_2$—OH, —OS(=O)$_2$OH when D represents

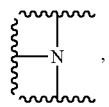 [SMILES: *N(*)*]

E can be absent.

It is surprising to observe that, with the help of a negative group, such as a carboxyl group, present in said motif, azide groups are perfectly pulled out to the surface of nanoparticles during nanoprecipitation, which makes it possible to be further reacted with nucleic acids bearing acetylene unit.

Figure 3:
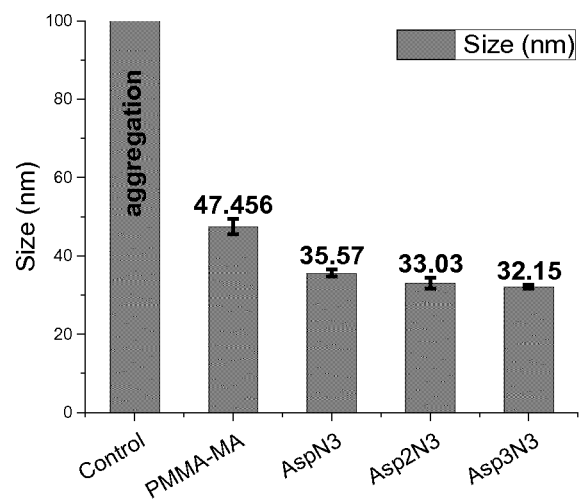

It is observed that in case of control polymer bearing azide group without a negative group, such as a carboxyl group, large aggregates were formed (FIG. 3). By contrast, polymers bearing the motif of formula (I) can produce nanoparticles with the size of 30-50 nm. Remarkably, with the increase in the number of carboxyl groups on the surface, the size of nanoparticles decreases.

Thus, one of the aspects of the present invention concerns a polymeric nanoparticle based on a modified hydrophobic polymer containing a motif of formula (I').

Said nanoparticle comprises:
a hydrophobic polymer, said chains bearing at least one motif of formula (I'),

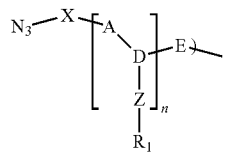

wherein:

A represents a spacer chosen from: —(CH$_2$)$_m$—, —(CH$_2$)$_p$NH—CO(CH$_2$)$_q$—, —(CH$_2$)$_p$CO—NH(CH$_2$)$_q$—, —(CH$_2$)$_p$O(CH$_2$)$_q$—, —(CH$_2$)$_p$NH(CH$_2$)$_q$O—, —(CH$_2$)$_m$CO—, —CO(CH$_2$)$_m$—, each of m, p and q represent independently from each other an integer chosen from 0 to 8, preferably an integer chosen from 0 to 5, more preferably an integer chosen from 0 to 3, D represents a group chosen from:

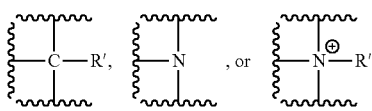

wherein R' represents a hydrogen, a halogen, a (C1-C8)alkyl,
a cyclo(C3-C7)alkyl eventually monosubstituted, a monocyclic non-aromatic heterocyclic group eventually monosubstituted, or a monocyclic aromatic group eventually monosubstituted, E represents $-(Y-NR_a)-$, where $R_a$ is H or a (C1-C8) alkyl, X, Y, Z are identical or different and each represent independently of the other a spacer chosen from $-(CH_2)_r-$, $-(CH_2-CH_2-O)_r-$, $-(CH_2-CH_2-NH)_r-$, $-(CH_2)_sNH-CO(CH_2)_t-$, $-(CH_2)_sCO-NH(CH_2)_t-$, wherein r, s and t represent independently from each other an integer chosen from 0 to 8, preferably an integer chosen from 0 to 5, more preferably an integer chosen from 0 to 3, n represents an integer chosen from 1 to 10, in particular 1 to 3, $R_1$ represents
—COOH,
—$PO(OH)_2$, —$PO(OR_b)OH$, —O—$PO(OH)_2$, —O—$PO(OR_b)OH$, where $R_b$ is methyl or ethyl,
—$S(=O)_2$—OH, —$OS(=O)_2OH$ when D represents

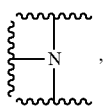

E can be absent,
said motif of formula (I) being bound to a carboxyl group of the polymer and being situated on the surface of the nanoparticle and
optionally, said polymeric nanoparticle comprising luminescent dyes.

Within the scope of the present invention, said luminescent dyes can be fluorescent dyes or phosphorescent dyes. Said luminescent dye can be an energy donor dye.

In particular embodiment, luminescent dyes are encapsulated in the nanoparticles of the invention.

In an another particular embodiment of the nanoparticle of the invention, the chains of hydrophobic polymer bear at least one motif of formula (I)

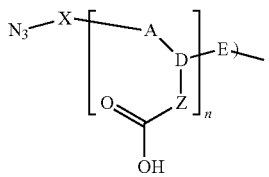

Wherein X, A, D, E, Z, n are defined as before.

A particular embodiment concerns a dye-loaded polymeric nanoparticle based on a modified hydrophobic polymer containing a motif of formula (I).

Said nanoparticle comprises:
a hydrophobic polymer, said chains bearing at least one motif of formula (I),

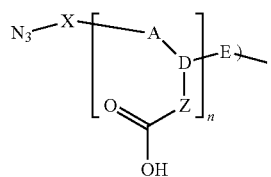

wherein:
A represents a spacer chosen from: $-(CH_2)_m-$, $-(CH_2)_pNH-CO(CH_2)_q-$, $-(CH_2)_pCO-NH(CH_2)_q-$, $-(CH_2)_pO(CH_2)_q-$, $-(CH_2)_pNH(CH_2)_qO-$, $-(CH_2)_mCO-$, $-CO(CH_2)_m-$, each of m, p and q represent independently from each other an integer chosen from 0 to 8, preferably an integer chosen from 0 to 5, more preferably an integer chosen from 0 to 3, D represents a group chosen from:

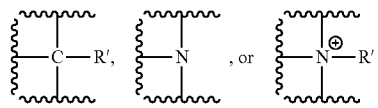

wherein R' represents a hydrogen, a halogen, a (C1-C8)alkyl,
a cyclo(C3-C7)alkyl eventually monosubstituted, a monocyclic non-aromatic heterocyclic group eventually monosubstituted, or a monocyclic aromatic group eventually monosubstituted, E represents $-(Y-NR_a)-$, where $R_a$ is H or a (C1-C8) alkyl, X, Y, Z are identical or different and each represent independently of the other a spacer chosen from $-(CH_2)_r-$, $-(CH_2-CH_2-O)_r-$, $-(CH_2-CH_2-NH)_r-$, $-(CH_2)_sNH-CO(CH_2)_t-$, $-(CH_2)_sCO-NH(CH_2)_t-$, wherein r, s and t represent independently from each other an integer chosen from 0 to 8, preferably an integer chosen from 0 to 5, more preferably an integer chosen from 0 to 3, n represents an integer chosen from 1 to 10, in particular 1 to 3, when D represents

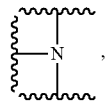

E can be absent;
said motif of formula (I) being bound to a carboxyl group of the polymer and being situated on the surface of the nanoparticle and
energy donors formed by a salt of at least one donor dye and bulky fluorinated anion, said energy donors being encapsulated in the hydrophobic polymer.

As used herein, the term "(C1-C8)alkyl" is meant to a branched or unbranched saturated hydrocarbon group having from 1 to 8 carbon atoms. Examples of "(C1-C8)alkyl" can be, but not limited to, methyl, ethyl, n-propyl, iso-propyl, n-butyl, sec-butyl, iso-butyl, tert-butyl, n-pentyl, isopentyl, neopentyl, n-hexyl, n-heptyl, n-octyl.

As used herein, the term "halogen" is meant to fluorine, chlorine, bromine or iodine.

The term "cyclo(C3-C7)alkyl", as used herein, is meant to a cyclic saturated carbon-based ring composed of from 3 to 7 carbon atoms. Examples of these cycloalkyl include cyclopropyl, cyclobutyl, cyclopentyl, cyclohexyl, cycloheptyl. Said cyclo(C3-C7)alkyl can comprise one substituent.

The term "monocyclic non-aromatic heterocyclic group", as used herein, is meant to a monocyclic saturated group which ring is formed by 3 to 10 atoms, wherein at least one atom besides carbon atoms is chosen from N, S, O. Said monocyclic non-aromatic heterocyclic group can comprise one substituent.

Examples of monocyclic non-aromatic heterocyclic groups that can be envisaged are pyrrolidine, piperidine, tetrahydrofuran, tetrahydropyran, thiolane.

The term "monocyclic aromatic group" as used herein is referred to an aromatic group consisting only of one conjugated planar ring. Said monocyclic aromatic group can be heterocyclic. Said monocyclic aromatic group can comprise one substituent.

Examples of monocyclic aromatic group likely to be used in the present invention include, but not limited to, phenyl, tolyl, phyridinyl, pyrazinyl, pyrimidinyl, pyridazynyl, pyrrolyl, thiophenyl, imidazolyl, oxazolyl, thiazolyl, pyrazolyl, furyl.

The term "D represents

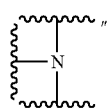

as used herein is referred to
D being a nitrogen atom on which A, Z, and E are directly bound, or
D being a cyclo group, such as a cyclo(C3-C7)alkyl, a monocyclic non-aromatic heterocyclic or a monocyclic aromatic group, bearing a nitrogen atom as substituent, said nitrogen atom being bound to E, at least one of A or Z being bound to said cyclo group. As examples are the following groups

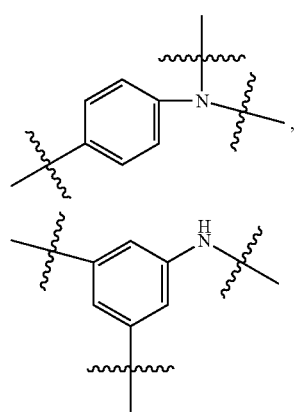

The term "one luminescent dye" is referred to a group of luminescent dyes which chemical structures are identical and have the same excitation spectra and emission spectra.

The term "one donor dye" is referred to a group of energy donor dyes which chemical structures are identical and have the same excitation spectra and emission spectra. The term "one donor dye" in any way is not meant to a single molecule by nanoparticle.

According to an embodiment, the dye-loaded hydrophobic polymeric nanoparticles of the present invention encapsulate at least two energy donor dyes.

A, X, Y, and Z are respectively a linear spacer, which would make it easier for nucleic acids bearing acetylene unit to approach azide groups.

In a particular embodiment, at least one carboxyl group of the hydrophobic polymer is bound with a motif of formula (Ia):

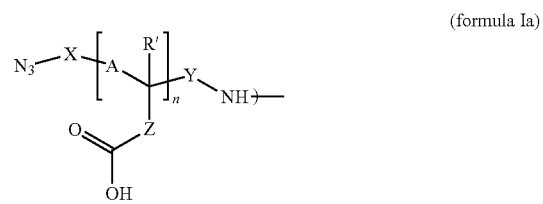

wherein A, X, Y, Z, n, R' are defined as before.

In a more particular embodiment, at least one carboxyl group of the hydrophobic polymer is bound with a motif of formula (Ib)

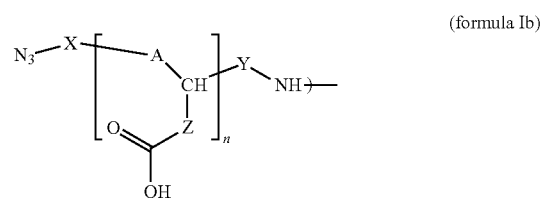

wherein A, X, Y, Z, n are defined as before.

In another particular embodiment, at least one carboxyl group of the hydrophobic polymer is bound with a motif of formula (Ic)

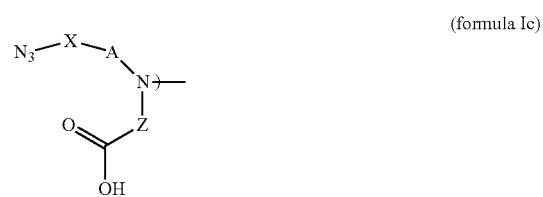

Wherein A, X, Z are defined as before.

In a preferred embodiment, the spacer A is chosen from: —NH—CO—, —CH$_2$—CH$_2$—, —CO—NH—, —CH$_2$—O—CH$_2$—, —CO—CH$_2$—CH$_2$—.

In another preferred embodiment, the spacers X and Z are composed of 1 to 3 methylene bridges and the spacer Y is absent.

In a still more particular embodiment, at least one carboxyl group of the hydrophobic polymer is bound with a motif of formula (Ib1)

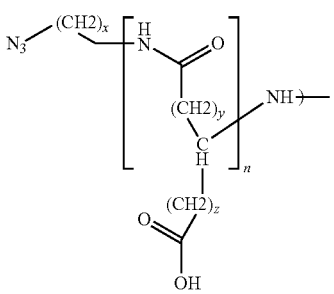

wherein x, y and z represent each an integer chosen from 0 to 8, preferably an integer chosen from 0 to 5, more preferably an integer chosen from 0 to 3.

Particular examples of motif of formula (Ib1) can be cited are:

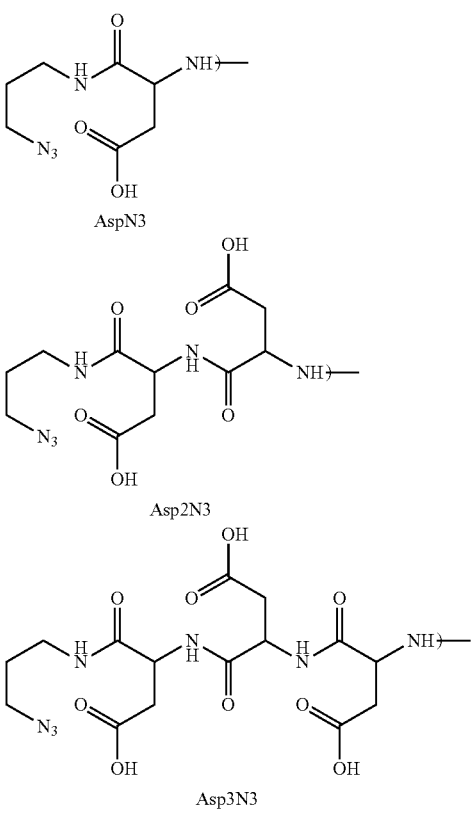

The hydrophobic polymer likely to be used in the present invention is chosen from polymethacrylates (e.g. PMMA-MA), aliphatic polyesters (e.g. PLGA or PCL) and polystyrene and derivatives thereof. Said suitable polymer should bear at least one carboxyl group on its chain.

The term "polymethacrylate" as used herein, means a polymer of salt or ester of polymethacrylic acid, which monomer can be represented by the formula —[(ROCO)C(Me)CH$_2$]—, wherein R is a hydrogen, an (C$_1$-C$_8$)alkyl, a cationic or a anionic group. Examples of polymethacrylates include, but are not limited to, poly(methyl methacrylate), poly(ethyl methacrylate), poly(butyl methacrylate).

According to the invention, a derivative of polymethacrylate means a polymethacrylate bearing one or more substitutions on its side chain. Said substitution can be an aliphatic group, hydrogen, aromatic group, an anionic or cationic group. Examples of derivative of polymethacrylate are poly(methyl methacrylate-co-methacrylic acid) (PMMA-MA), poly(methyl methacrylate-co-2-methacrylamidoethanesulfonic acid) (PMMA-SO3).

The term "polystyrene" as used herein, means an aromatic polymer synthetized from the monomer which is styrene, or a derivative of styrene.

According to the invention, a derivative of polystyrene means a polystyrene bearing one or more substitutions on its side chain. Said substitution can be an anion, such as a sulfonate, phosphate, phosphonate, phosphoryl, and carboxyl, or a cation, such as a quaternary ammonium, or a tertiary ammonium. Examples of derivative of polystyrene can be polystyrene sulfonates, polystyrene phosphonate, carboxypolystyrene.

The term "aliphatic polyester" as used herein, means a group of aliphatic polymers containing ester functional group in the repeat units of main chain. Examples of aliphatic polyesters can be cited as, but are not limited to, polycaprolactone (PCL), poly(lactic acid) (PLA), poly(glycolic acid) (PGA), poly(lactide co-glycolide) (PLGA).

The first criteria for choosing a suitable polymer is that polymer's matrix could ensure appropriate distribution of the dyes with high brightness and efficient excitation energy transfer (EET).

By the way, said polymer should produce rather small nanoparticles to insure an efficient FRET, since the efficiency of FRET is determined by the distance between the energy donor dye(s) and the energy acceptor dye, the longer the distance, the lower the FRET efficiency.

Thirdly, in order to control the number of azide groups being introduced on surface of nanoparticle, and further to control the number of acceptor dyes being attached on surface of nanoparticle, the hydrophobic polymer likely to be used in the present invention is a polymer containing about from 0.1 to 10 molar percent, in particular 1-2 molar percent, of carboxyl groups.

In a preferred embodiment, said polymer is poly(methyl methacrylate-co-methacrylic acid) and derivatives thereof.

Example of derivatives of PMMA can be cited is poly(methyl methacrylate-co-methacrylic acid) (PMMA-MA, 1.6% methacrylic acid, Mn ~15000, Mw ~34000).

According to an embodiment of the present invention, the content of energy donor in an aforementioned nanoparticle is from 5 to 700 mmol/kg, in particular from 50 to 300 mmol/kg, more in particular 170 mmol/kg with respect to the total mass of the nanoparticles.

Said dye-loaded hydrophobic polymeric nanoparticles can be obtained by nanoprecipitation from an organic solvent containing:
 a hydrophobic polymer said chains bearing at least a motif of formula (I') or (I), and
 at least one luminescent dye, which can be in particular one energy donor dye and bulky fluorinated anion.

Said solution in organic solvent can be a mixture of a hydrophobic polymer that bears at least a motif of formula (I') or (I) and a hydrophobic polymer without any motif of formula (I') or (I).

Examples of organic solvents that can be used in nanoprecipitation are acetonitrile, tetrahydrofurane, dioxane, acetone, dimethylformamide, dimethylsulfoxide.

Another aspect of the present invention is to provide an oligonucleotide-functionalized hydrophobic polymer nanoparticle, said nanoparticle being a hydrophobic polymeric nanoparticle as described above, wherein at least a part of azide groups are transformed into triazole groups or a derivative thereof and being functionalized by:
 (a) target-specific oligonucleotides, and/or
 (b) non-specific oligonucleotides.

Another embodiment of the invention concerns an oligonucleotide-functionalized hydrophobic polymer nanoparticle comprising one energy donor dye, said nanoparticle being a hydrophobic polymeric nanoparticle as described above, wherein at least a part of azide groups are transformed into triazole groups or a derivative thereof and being functionalized by:
 (a) target-specific oligonucleotides, and/or
 (b) non-specific oligonucleotides.

Another aspect of the present invention is to provide an oligonucleotide-functionalized hydrophobic polymer nanoparticle comprising at least one energy donor dye and at least one energy acceptor dye,
 said nanoparticles being:
  a dye loaded polymeric nanoparticle described above, wherein at least a part of azide groups are transformed into triazole groups or a derivative thereof and being functionalized by:
   (a) target-specific oligonucleotides, and/or
   (b) non-specific oligonucleotides,
wherein the energy acceptor dye is conjugated to the target-specific oligonucleotide which forms a hairpin loop structure or to a separated target-competitive oligonucleotide which forms a double-stranded complex with at least a part of target-specific oligonucleotide, and
wherein the molar ratio between target-specific oligonucleotides and non-specific oligonucleotides is from 1:1 to 1:1000, in particular from 1:3 to 1:10, more particularly 1:6.

Within the meaning of the present invention, the term "oligonucleotide-functionalized hydrophobic polymer nanoparticle", the term "oligonucleotide-functionalized nanoparticle" and the term "nanoprobe" are interchangeable.

The diameter of the nanoparticles of the present invention is varied from 10 nm to 300 nm, preferably in the range from 20 nm to 100 nm, more preferably in the range from 25 to 70 nm, still more preferably in the rage from 30 to 50 nm. Nanoparticle's diameter can be measured according to a conventional method by electron microscopy.

The nanoparticles of the present invention have a rather small size compared to nanoparticles previously described by Chad Mirkin and Omid C. Farokhzad groups containing PEG chain as linker between carboxyl group and main polymeric chain.

It is already known that the distance between donor dyes and acceptors dyes is extremely important for the energy transfer efficiency (which is dependent on the distance to the 10 power of −6). Small size of the nanoparticles and of the linkers (between polymer and oligonucleotide) of the present invention ensures that acceptor dyes are localized close to the nanoparticles surface to enable efficient Forester Resonance Energy Transfer (FRET) between donor dyes and acceptors dyes.

In oligonucleotide-functionalized nanoparticle of the present invention, the molar ratio between the energy acceptor and energy donor is from 1:10 to 1:1000, in particular 1:100.

Said nanoparticle contains respectively:
 from 5 to 700 mmol/kg, in particular from 50 to 300 mmol/kg, more in particular 170 mmol/kg of donor dyes with respect to the total mass of the nanoparticles, and
 from 1 to 500, in particular from 1 to 100, more particularly about 20 acceptor dyes on nanoparticle surface.

Due to small particle size and the presence of huge number of donor dyes inside a particle, the oligonucleotide-functionalized nanoparticle of the present invention can work as nano-antenna to amplify fluorescence. The term "nano-antenna" is meant here to a nanoparticle that can harvest light energy with a huge number of energy donors and effectively transfer this energy to few energy acceptors within the nanoparticle and, therefore, can amplify the fluorescence emission of the acceptor. The oligonucleotide-functionalized nanoparticle of the present invention can amplify >50 times the fluorescence that could be directly produced between a donor dye and an acceptor dye, a value that has not been achieved to date with any optical probes for detection of biomolecules, being comparable or better than equivalent probes based on plasmon-enhanced fluorescence.

By "oligonucleotide" is meant a short single-stranded DNA or RNA. An oligonucleotide comprised in oligonucleotide-functionalized nanoparticles of the present invention may be a synthetic oligonucleotide, whose sequence can be designed with the help of conventional sequence design software. Within meaning of the present invention, said oligonucleotide is constituted by 5 to 50 nucleotides.

Oligonucleotides are attached to a dye-loaded polymeric nanoparticle as described above for two purposes: the first one is to further stabilize a hydrophobic polymer nanoparticle in aqueous solution, the second one is to provide a support structure for an acceptor dye.

By "non-specific oligonucleotide" is meant to an oligonucleotide which sequence is neither complementary to that of a target biomolecule of type nucleic acid nor recognized by a biomolecule such as protein or toxin. The essential function of non-specific oligonucleotide is to provide further nanoparticles stability in solution. It is observed that nanoparticles bearing non-specific oligonucleotides on surface can be stable in solution at 4° C. during at least 2 months after the preparation.

According to a particular embodiment, the non-specific oligonucleotides are non-coding oligonucleotides.

According to another particular embodiment, the non-specific oligonucleotides are poly(dA) or poly(dT) of 10 to 50 nucleotides.

By "target-specific oligonucleotide" is meant to an oligonucleotide which sequence is complementary to that of a target biomolecule of type nucleic acid or is recognized by a biomolecule, such as a protein or a toxin. The target-specific oligonucleotide confers target specificity to each oligonucleotide-functionalized nanoparticle, since it is the target-specific oligonucleotide that is recognized by a target biomolecule and forms with the latter a stable complex. The nucleic sequence of a target-specific oligonucleotide depends on the target biomolecule to be detected. A target-specific oligonucleotide either forms a double-stranded oligonucleotide with said target biomolecule or forms an aptamer/target complex.

Within the meaning of the present invention, that a first oligonucleotide is complementary to a second oligonucleotide means that a first oligonucleotide has at least 5 consecutive sequence matches with a second oligonucleotide and has less than 3 sequence mismatches.

According to a particular embodiment, the target-specific oligonucleotide is constituted by 10 to 40 nucleotides. According to an embodiment, a target-specific oligonucleotide can be bound to an acceptor dye. The latter can be situated on one end of the oligonucleotide which is opposite to the end by which is bound to the polymer.

In this case, nucleic sequence of said target-specific oligonucleotide is designed to form a hairpin loop structure to bring the acceptor dye close to the surface of the nanoparticle.

The target-specific sequence can be situated in the part of loop sequence of a hairpin loop structure.

The target-specific sequence can also be situated in a part of the stem sequence. In this case, said target-specific oligonucleotide contains also a target-competitive sequence in another part of the stem sequence. In another word, target-competitive oligonucleotide and target-specific oligonucleotide can be two parts situated in the same oligonucleotide.

According to another embodiment, an acceptor dye is attached to a separated target-competitive oligonucleotide. Said target-competitive oligonucleotide brings acceptor dye close to the surface of the nanoparticle by annealing with the target-specific oligonucleotide.

By "target-competitive oligonucleotide" is meant to an oligonucleotide which sequence is complementary to that of the target-specific oligonucleotide carried on the same nanoparticle. When the target biomolecule is a nucleic acid, the sequence of target-competitive oligonucleotide is identical to at least a part of that of the biomolecule.

According to a particular embodiment, in order to insure that the target-specific oligonucleotide forms a more stable complex with target biomolecule than with the target-competitive oligonucleotide, the target-competitive oligonucleotide is shorter than the target-specific oligonucleotide and is constituted by 5 to 20 nucleotides.

Thanks to high brightness produced by unprecedented antenna effect, the oligonucleotide-functionalized nanoparticles of the present invention enable to decrease the limit of detection of a nucleic acid at least to 5 pM, which is ~1000 fold higher than that achieved using molecular probes. That is one of the lowest limit of detection that has been achieved by an optical DNA probe without exploiting molecular multiplication. This high sensitivity makes these oligonucleotide-functionalized nanoparticles useful as a biosensor for directly detecting a biomolecule present in a sample.

Thus, another aspect of the present invention concerns the oligonucleotide-functionalized hydrophobic polymer nanoparticles as described above for its uses as biosensor for a target biomolecule.

In a further aspect, the present invention concerns a biosensor comprising or consisting of an oligonucleotide-functionalized hydrophobic polymer nanoparticle of the present invention.

The biosensor of the present invention indicates the presence of a target biomolecule by signal-off FRET fluorescence, that-is-to-say a decrease or even disappearance of FRET fluorescence. In fact, when a target biomolecule is in contact with said nanoparticle bearing a target-specific oligonucleotide, the latter dehybridizes with the target-competitive oligonucleotide and forms a more stable complex with the target biomolecule. Therefore, the separated target-competitive oligonucleotides comprising an acceptor dye are released from the surface of oligonucleotide-functionalized nanoparticles and acceptor dye becomes far from the donor dye. This farther distance leads to the decrease till disappearance of FRET fluorescence. Very similar effect is achieved when the acceptor dye is attached to the target-specific oligonucleotide which forms a hairpin loop structure. In this case, hybridization with the target opens the hairpin, thus increasing the distance between the acceptor dye and the donor particle.

According to the present invention, said target biomolecules can be single-stranded DNAs, RNAs, mRNAs, microRNAs, siRNAs, satellite RNAs, DNA type or RNA type synthetic oligonucleotide, cDNAs, PCR amplified products, fragments of genomic DNA, a protein or a toxin.

Within the meaning of the present invention, the term "target biomolecule" and the term "biomolecule of interest" are interchangeable.

When the biomolecule of interest is a nucleic acid type biomolecule, the complex formed by said biomolecule and the target-specific oligonucleotide is a double-stranded complex. In another word, the target-specific oligonucleotide has a sequence complementary to at least a part of that of said biomolecule.

When the biomolecule of interest is a protein or a toxin, the complex formed by said biomolecule and the target-specific oligonucleotide is an aptamer-protein/toxin complex. The target-specific oligonucleotide is folded into an aptamer capable of binding non-covalently with high affinity and specificity to a target protein or a toxin. The sequence of said oligonucleotide can be determined by the general knowledge of a skilled person in the art, for example by SELEX technique (Systematic evaluation of ligands by exponential enrichment).

In a particular embodiment, the target biomolecule is a nucleic acid target of >10 nucleotides chosen from a microRNA, a mRNA, a siRNA, a ssDNA, or a cDNA.

The present invention concerns another aspect that is to provide a method for in vitro detecting a biomolecule of interest in a sample.

Said method comprises the step of:
  contacting a sample containing a biomolecule of interest with above-mentioned oligonucleotide-functionalized hydrophobic polymer nanoparticle,
  forming a composition wherein the target biomolecule binds to the oligonucleotide-functionalized hydrophobic polymer nanoparticle,
  measuring the fluorescence changes produced by changes in the Forster Resonance Energy Transfer (FRET) between the donor dyes of nanoparticle and the acceptor dyes.

The nanoprobe can detect the target biomolecule in solution or directly in a biological sample (cells in culture, biological tissues). For the detection, the nanoprobe can be suspended in solution or immobilized on surfaces of microplates.

Said sample can be a sample obtained from biological fluid, from an in vitro cell culture or from a tissue, from plants, from microorganisms, a solution containing biological molecules, an environmental sample, a food sample, a pharmaceutical sample.

By "biological fluid" is meant to a liquid contained, excreted or secreted from a living animal or plant, for example: blood, different fraction of blood, lymph, bile, saliva, exudates. In a preferred embodiment of the present invention, the biological fluid is a human or animal origin fluid chosen from serum, inactivated serum, plasma, or blood.

By "tissue" is meant to a human, animal or vegetal tissue. In a particular embodiment of the invention, the sample of a tissue is a sample obtained by biopsy or during surgical operation. In a more particular embodiment, the tissue is a tumoral tissue obtained by biopsy or during surgical operation from a patient suffering from a cancer, or suspected to develop a cancer.

Many proteins, antibodies, microRNA, siRNA are already known to be biomarkers of pathological conditions. Because of their very low limit of detection, the oligonucleotide-functionalized nanoparticles of the present invention are particularly suitable to be used as biosensor for these biomarker in the in vitro diagnostic methods of diseases.

Oligonucleotide-functionalized nanoparticles of the present invention can also be used as biosensor for detecting the presence of a toxic compound or a pathogenic microorganism in an environmental sample, a food sample or a pharmaceutical sample.

By "environmental sample" is meant to a sample collected from an environment, such as soil, sludge, or waste water.

According to another aspect, the invention concerns oligonucleotide-functionalized nanoparticles as described above for its use as a contrast agent, a diagnostic agent or as medical imaging agent.

The present invention concerns also a pharmaceutical composition comprising oligonucleotide-functionalized hydrophobic polymer nanoparticles as described above for its use as a contrast agent, a diagnostic agent or as medical imaging agent.

Said composition can be used as an in vivo diagnostic agent.

Said nanoparticles can be formulated into a pharmaceutical composition, according to conventional drug formulation methods. Suitable pharmaceutical vehicles can be comprised in said compositions.

For example, said pharmaceutical composition can be an injectable pharmaceutical composition.

One of the aspects of the present invention is also to provide a method for conjugating an oligonucleotide to a hydrophobic polymer nanoparticle, said method comprising:

(i) reacting a hydrophobic polymer bearing at least a carboxyl group with a compound of formula (II'),

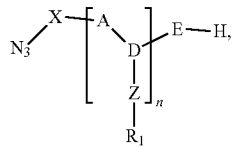

Formula (II')

wherein

A represents a spacer chosen from: —(CH$_2$)$_m$—, —(CH$_2$)$_p$NH—CO(CH$_2$)$_q$—, —(CH$_2$)$_p$CO—NH(CH$_2$)$_q$—, —(CH$_2$)$_p$O(CH$_2$)$_q$—, —(CH$_2$)$_p$NH(CH$_2$)$_q$O—, —(CH$_2$)$_m$CO—, —CO(CH$_2$)$_m$—, each of m, p and q represent independently from each other an integer chosen from 0 to 8, preferably an integer chosen from 0 to 5, more preferably an integer chosen from 0 to 3, D represents a group chosen from:

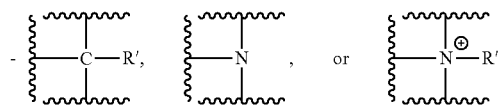

wherein R' represents a hydrogen, a halogen, a (C1-C8)alkyl, a cyclo(C3-C7)alkyl eventually monosubstituted, a monocyclic non-aromatic heterocyclic group eventually monosubstituted, or a monocyclic aromatic group eventually monosubstituted, E represents —(Y—NR$_a$)—, where R$_a$ is H or an (C1-C8) alkyl, X, Y, Z identical or different and each represent a spacer chosen from —(CH$_2$)$_r$—, —(CH$_2$—CH$_2$—O)$_r$—, —(CH$_2$—CH$_2$—NH)$_r$—, —(CH$_2$)$_s$NH—CO(CH$_2$)$_t$—, —(CH$_2$)$_s$CO—NH(CH$_2$)$_t$—, r, s and t represent independently from each other an integer chosen from 0 to 8, preferably an integer chosen from 0 to 3;

R$_1$ represents:

—COOH, eventually protected by a carboxyl protecting group, such tert butyl group, —PO(OH)$_2$, —PO(OR$_b$)OH, —O—PO(OH)$_2$, —O—PO(OR$_b$)OH, where R$_b$ is methyl or ethyl,

—S(=O)$_2$—OH, —OS(=O)$_2$OH n represents an integer chosen from 1 to 10, in-particular 1 to 3, when D represents

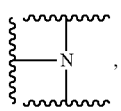

E can be absent, to obtain a modified polymer, said chains bearing at least one motif of formula (I')

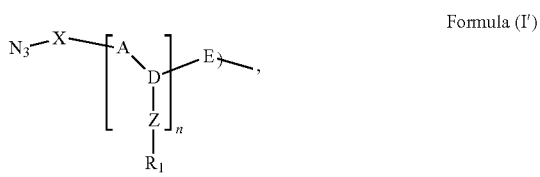

Formula (I')

wherein A, D, X, Z, E, R$_1$ and n are as defined above, (ii) precipitating the modified polymer obtained in step (i) from an organic solvent into aqueous solution to produce the nanoparticles;

(iii) carrying out a cycloaddition between the nanoparticles obtained in the previous step with:

(a) a non-specific oligonucleotide bearing a functional group capable of reacting with the azide group of motif (I) by a cycloaddition and/or (b) a target-specific oligonucleotide bearing a functional group capable of reacting with the azide group of motif (I) by a cycloaddition.

Thanks to the development of the compound of formula (II') as linker, azide group as functional groups and carboxyl group are on the same time directly introduced into commercially available classical hydrophobic polymers.

In a particular embodiment, said method comprises:

(i) reacting a hydrophobic polymer bearing at least a carboxyl group with a compound of formula (II),

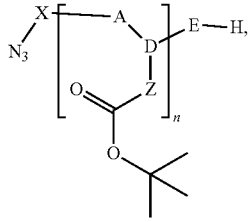

Formula (II)

wherein

A represents a spacer chosen from: —(CH$_2$)$_m$—, —(CH$_2$)$_p$NH—CO(CH$_2$)$_q$—, —(CH$_2$)$_p$CO—NH(CH$_2$)$_q$—, —(CH$_2$)$_p$O(CH$_2$)$_q$—, —(CH$_2$)$_p$NH(CH$_2$)$_q$O—, —(CH$_2$)$_m$CO—, —CO(CH$_2$)$_m$—, each of m, p and q represent independently from each other an integer chosen from 0 to 8, preferably an integer chosen from 0 to 5, more preferably an integer chosen from 0 to 3, D represents a group chosen from:

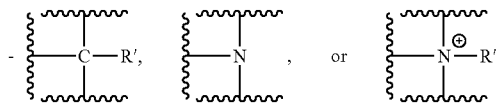

wherein R' represents a hydrogen, a halogen, a (C1-C8)alkyl, a cyclo(C3-C7)alkyl eventually monosubstituted, a monocyclic non-aromatic heterocyclic group eventually monosubstituted, or a monocyclic aromatic group eventually monosubstituted, E represents —(Y—NR$_a$)—, where R$_a$ is H or an (C1-C8) alkyl, X, Y, Z identical or different and each represent a spacer chosen from —(CH$_2$)$_r$—, —(CH$_2$—CH$_2$—O)$_r$—, —(CH$_2$—CH$_2$—NH)$_r$—, —(CH$_2$)$_s$NH—CO(CH$_2$)$_t$—, —(CH$_2$)$_s$CO—NH(CH$_2$)$_t$—, r, s and t represent independently from each other an integer chosen from 0 to 8, preferably an integer chosen from 0 to 3;

n represents an integer chosen from 1 to 10, in-particular 1 to 3, when D represents

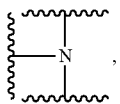

E can be absent, to obtain a modified polymer, said chains bearing at least one motif of formula (I)

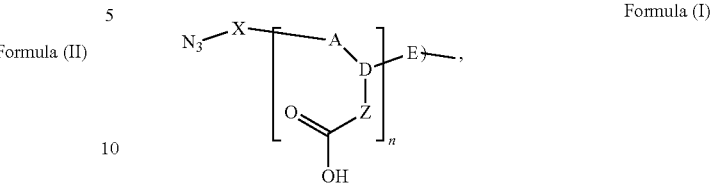

Formula (I)

wherein A, D, X, Z, E and n are as defined above, (ii) precipitating the modified polymer obtained in step (i) from an organic solvent into aqueous solution to produce the nanoparticles;

(iii) carrying out a cycloaddition between the nanoparticles obtained in the previous step with:

(c) a non-specific oligonucleotide bearing a functional group capable of reacting with the azide group of motif (I) by a cycloaddition (d) a target-specific oligonucleotide bearing a functional group capable of reacting with the azide group of motif (I) by a cycloaddition.

Contrary to the method described by Chad Mirkin group, the step (i) of above-described method does not need high salt concentration.

The step of precipitation can be carried out by a conventional method for nanoparticle precipitation.

The modified polymer obtained in step (i) can be co-precipitated with luminescent dyes, for example a salt of at least one donor dye and bulky fluorinated anion, to encapsulate luminescent dyes into the nanoparticles.

Target-specific oligonucleotides and non-specific oligonucleotides are bound to a dye-loaded hydrophobic nanoparticle obtained in step (ii) by a triazole group or a derivative thereof which is formed by a cycloaddition between:

the azide group of a dye-loaded polymeric nanoparticle obtained in step (ii), and
a functional group capable of reacting with azide by a cycloaddition comprised in a target-specific oligonucleotide and in a non-specific oligonucleotide Said functional group can be any functional group known in prior art capable of reacting with azide by a cycloaddition.

In particular, said functional group is chosen from:
(C7-C10) cycloalkynyl group
heterocyclic alkynyl group, and
(C2-C10)alkynyl group The term "(C7-C10)cycloalkynyl group", as used herein, refers to a cyclic unsaturated carbon-based ring composed of from 7 to 10 carbon atoms and containing at least a triple bond between two carbon atoms. Examples of (C-C10) cycloalkynyl group are cycloheptynyl, cyclooctynyl, cyclononynyl, cyclodecynyl.

In particular, such cycloalkynyl group can be cyclooctynyl group or derivatives thereof, among which we can cite biarylazacyclooctynone (BARAC), dibenzocyclooctynyl (DBCO), monofluorinated cyclooctynyl (MOFO), difluorinated cyclooctynyl (DIFO), ALO(aryl-less octynyl), dimethoxyazacyclooctynyl (DIMAC), and difluorobenzocyclooctynyl (DIFBO).

The term "heterocyclic alkynyl group" is referred to a monocyclic non-saturated group which ring is formed by 3 to 10 atoms and contains at least an carbon-carbon triple bond, wherein at least one atom besides carbon atoms is chosen from N, S, O.

The term "(C2-C10)alkynyl group", as used herein, refers to a branched or unbranched hydrocarbon group of having 2 to 10 carbon atoms comprising at least a triple bond between two carbon atoms. Examples of alkynyl groups include ethynyl, propynyl, butynyl, octynyl, nonynyl, decynyl etc. Said alkynyl group can particularly comprise a terminal triple bond.

By "cycloaddition" is meant to any type of cycloaddition known in prior art, for example Diels-Alder cycloaddition, cupper-catalysed or cupper-free cycloaddition, etc.

It is preferred that cycloaddition between target-specific probe/non-specific probe and a dye-loaded hydrophobic nanoparticle is a cupper-free cycloaddition, because of its reliability, biocompatibility and minimal potential damage for the oligonucleotides and the nanoparticle.

For the effective reaction between an oligonucleotide and the dye-loaded nanoparticles, the organic solvent may be evaporated after the nanoprecipitation of nanoparticles and before the step (iii), which could be helpful to achieve micromolar concentrations of functional groups.

In a particular embodiment, said compound is of formula (IIa)

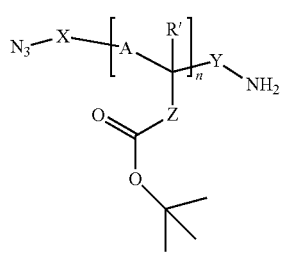

Formula (IIa)

wherein A, X, Y, Z, Y, n, R' are defined as that for formula (II).

In another particular embodiment, said compound is of formula (IIb)

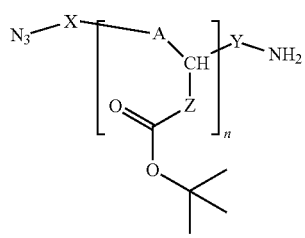

Formula (IIb)

wherein A, X, Y, Z, Y, n, are defined as that for formula (II).

In another particular embodiment, said compound is of formula (IIc)

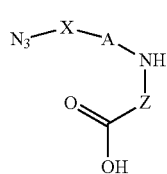

Formula (IIc)

Wherein A, X, Z are defined as that form formula (II).

In a preferred embodiment, said linker compound is represented by the formula (IIb1):

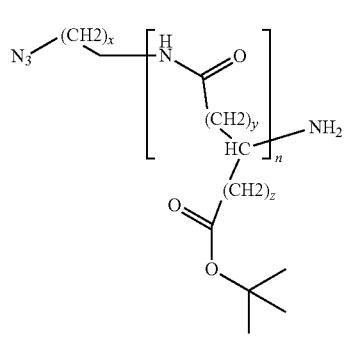

Formula (IIb1)

wherein x, y and z represent each an integer chosen from 0 to 5, preferably an integer chosen from 0 to 3.

In a more preferred embodiment, said compound can be for example one of following compounds.

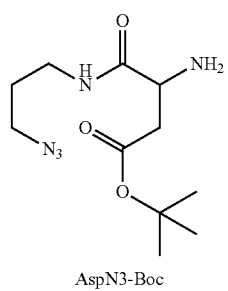

AspN3-Boc

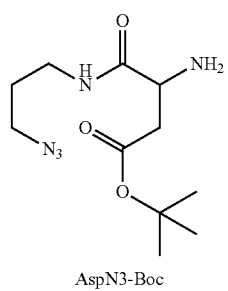

Asp2N3-Boc

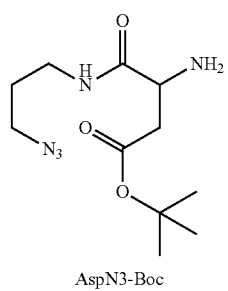

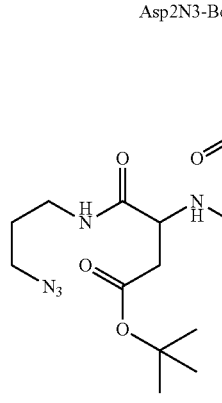

Asp3N3-Boc

In an additional aspect, the present invention provides also a kit for producing a biosensor as defined before. Said kit comprises:
- a dye-loaded polymeric nanoparticle as described above,
- a non-specific oligonucleotide bearing a functional group capable of reacting with an azide group by a cycloaddition Said kit provides to end-users a platform from which it is easy to personalize their oligonucleotide-functionalized nanoparticles according to their target biomolecules.

The end-user only need to design:
- a target-specific oligonucleotide of 10 to 40 nucleotides bearing a functional group capable of reacting with azide by a cycloaddition, and
- a target-competitive oligonucleotide of 5 to 20 nucleotides bearing an acceptor dye.

The end-user can also design a target-specific oligonucleotide bearing:
- a functional group capable of reacting with azide by a cycloaddition on one end of oligonucleotide, and
- an acceptor dye on another end of oligonucleotide, wherein the target-specific oligonucleotide can form a hairpin loop structure.

Energy Donor

In the oligonucleotide-functionalized nanoparticles of the present invention, the energy donor is formed by a salt of a donor dye and bulky fluorinated anion and is encapsulated in the matrix of the polymer.

As used herein, the term "encapsulated" is meant to enclose an energy donor inside the matrix of polymer.

By "donor dye" is meant to a luminescent material which, in its electronic excited state, may transfer energy to an energy acceptor.

The donor dye is chosen from a rhodamine derivative or a cyanine derivative.

In accordance with present invention, the donor dye can be a rhodamine of formula (A):

Formula (A)

In the above formula (A):
$R_1$, $R_2$, $R_3$ and $R_4$ are identical or different and each represent a hydrogen or a (C1-C8) alkyl group,
$R_5$ is a (C1-C24) alkyl.

The term "(C1-C8) alkyl group" as used herein, means a saturated straight or branched hydrocarbon chain containing from 1 to 8 carbons. Representative examples of (C1-C8) alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl.

The term "(C1-C24) alkyl group" is referred to a saturated straight or branched hydrocarbon chain containing from 1 to 24 carbons. Examples of (C1-C24) alkyl group can be, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, n-docenyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl.

Preferably, the rhodamine used in the present invention can rhodamine B octadecyl ester of formula (A1) hereafter.

(A1)

The donor dye can be also a cyanine derivatives of formulas (B1) and (B2).

Formula B1 and B2

$B_1$ $B_2$ wherein
n is a integer chosen from 0, 1, 2 or 3,
G is a substituted carbon, preferably —C(CH$_3$)$_2$ or a heteroatom O, S, N.
$R_1'$ and $R_3'$ are identical or different and represent each a (C1-C24) alkyl group.
$R_2'$ and $R_4'$ are identical or different and represent each a hydrogen or (C1-C24) alkyl group.

A compound of formula (B1), wherein n=1, corresponds to a Cy3 dye. An example of Cy3 dye is 1,1'-Dioctadecyl-3,3,3',3'-Tetramethylindocarbocyanine (DiI).

A compound of formula (B1), wherein n=2, corresponds to a Cy5 dye. An example of Cy5 dye is 1,1'-Dioctadecyl-3,3,3',3'-Tetramethylindodicarbocyanine (DiD).

A compound of formula (B1), wherein n=3, corresponds to a Cy7 dye. An example of Cy7 dye is 1,1'-Dioctadecyl-3,3,3',3'-Tetramethylindotricarbocyanine (DiR).

A compound of formula (B2), wherein n=1, corresponds to a Cy3.5 dye. An example of Cy3.5 dye is 1,1'-Dioctadecyl-3,3,3',3'-Tetramethylbenzindocarbocyanine.

A compound of formula (B2), wherein n=2, corresponds to a Cy5.5 dye. 1,1'-Dioctadecyl-3,3,3',3'-Tetramethylbenzindodicarbocyanine is an example of Cy5.5.

A compound of formula (B2), wherein n=3, corresponds to a Cy7.5 dye. 1,1'-Dioctadecyl-3,3,3',3'-Tetramethylbenzindotricarbocyanine is an example of Cy7.5.

The term "bulky fluorinated anions" as used herein is a large organic anion bearing aromatic and/or aliphatic fluorinated residues. Said bulky fluorinated anions work not only as counterion in energy donor but also as a spacer between the donor dyes that, on one hand, prevents their aggregation and self-quenching and, on the other hand, brings the energy donor dyes in very close proximity to enable ultrafast diffusion of excitation energy with minimal loss.

According to a particular embodiment of the present invention, the bulky fluorinated anion is chosen from tetrakis(pentafluorophenyl)borate (F5-TPB), tetrakis[3,5-bis-(trifluoromethyl)phenyl]borate (F6-TPB), tetrakis[3,5-bis-(1,1,1,3,3,3-hexafluoro-2-methoxy-2-propyl)phenyl]borate (F12-TPB) and tetrakis[perfluoro-tert-butoxy]aluminate (F9-Al).

Energy Acceptor

The energy acceptor is attached to an oligonucleotide-functionalized nanoparticle of the present invention by a target-specific oligonucleotide or by a target-competitive oligonucleotide.

By "acceptor dye" is meant a material, which can physically be excited by the energy transferred from a donor dye. The emission spectra of an acceptor dye should be at least 20 nm shifted to the longer wavelength.

The acceptor dye carried by a nanoparticle of the present invention can be an organic fluorophore, such as fluorescein-, rhodamine- or cyanine-based dyes (e.g. Cy3, Cy3.5 Cy5, Cy5.5, Cy7, Cy7.5), or a non-fluorescent dark quencher or a combination thereof.

As fluorescent acceptor dye commercial derivatives can be used: Alexa Fluor® (absorption maximum: 433-790 nm), e.g. Alexa Fluor® 647; Atto® (absorption maximum: 425-740 nm), e.g. Atto® 655; Abberior® (absorption maximum: 432-638 nm), e.g. Abberior® STAR RED; Dy® (absorption maximum: 430-831 nm), e.g. Dy® 654; Eterneon™ (absorption maximum: 480-680 nm), e.g. Eterneon™ Red 645; Chromeo™ (absorption maximum: 488-642 nm), e.g. Chromeo™ 642; Oyster® (absorption maximum: 488-680 nm), e.g. Oyster® 650.

A "non-fluorescent dark quencher" refers to a material which does not emit fluorescence in excited-state. Examples of non-fluorescent dark quencher to be cited is dabsyl (dimethylaminoazobenznesulfonic acid), dabcyl (4-(4-dimethylaminophenylazo)benzoic acid), Black Hole Quencher®-1, Black Hole Quencher®-2, Black Hole Quencher®-3, Atto® Q (e.g. Atto® MB2), Dy®Q (e.g. Dy®Q 660).

In an embodiment of the present invention, when the energy donor dye is a cyanine derivative of formula (B1 and B2), the energy acceptor dye is selected according to the following rule. The absorption spectrum of the acceptor should overlap with the emission spectrum of the donor dyes. As an example, the donor dye can be ocdadecyl-rhodamine B dye with F5-TPB counterion, while energy acceptor is Cy5 dye (2-((1E,3E,5Z)-5-(1-(3-hydroxypropyl)-3,3-dimethylindolin-2-ylidene)penta-1,3-dien-1-yl)-3,3-dimethyl-1-(3-(phosphonooxy)propyl)-3H-indol-1-ium).

An example of an acceptor dye bound to an oligonucleotide is given below.

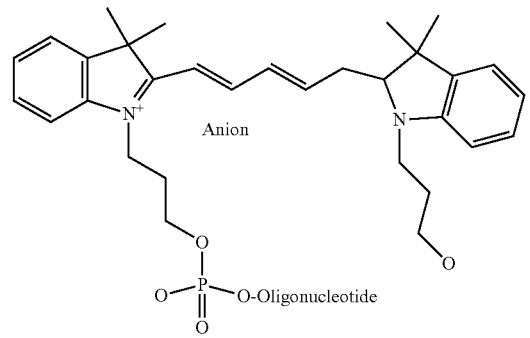

The conjugation between an acceptor dye and an oligonucleotide can also be carried on any suitable position, including aromatic ring of the acceptor dye.

Multiple Targets Detection

According to an embodiment, the oligonucleotide-functionalized nanoparticles of the present invention comprises more than one target-specific oligonucleotides, which are recognized by more than one target biomolecules different from each other.

By "one target-specific oligonucleotide" is meant to a group of target-specific oligonucleotide having the same nucleic acid sequence and being recognized by a same target biomolecule.

Said oligonucleotide-functionalized nanoparticles can be used as a biosensor for multiple target detections.

In order to indicate at the same time the presence of more than one target biomolecule, the oligonucleotide-functionalized nanoparticles of the present invention comprises also more than one acceptor dyes, whose number is identical to the number of target-specific oligonucleotides.

By "one acceptor dye" is meant to a group of energy acceptor dyes which chemical structures are identical and have the same excitation spectra and emission spectra. The term "one acceptor dye" in any way is not meant to a single molecule per nanoparticle.

When an oligonucleotide-functionalized nanoparticles comprises more than one acceptor dyes, the criteria for choosing suitable acceptor dyes is that their emission spectra are not over-lapped.

According to an embodiment of oligonucleotide-functionalized nanoparticle for its use in multiple target detections, said nanoparticle comprises one donor dye and more than one acceptor dyes. The emission spectrum of said donor dye covers the absorption spectra of those acceptors dyes.

The present invention is illustrated in more detail by following figures and examples

FIGURES

FIG. 1: Concept of oligonucleotide-functionalized hydrophobic polymer nanoparticle for amplified detection of nucleic acids.

Figure 2:
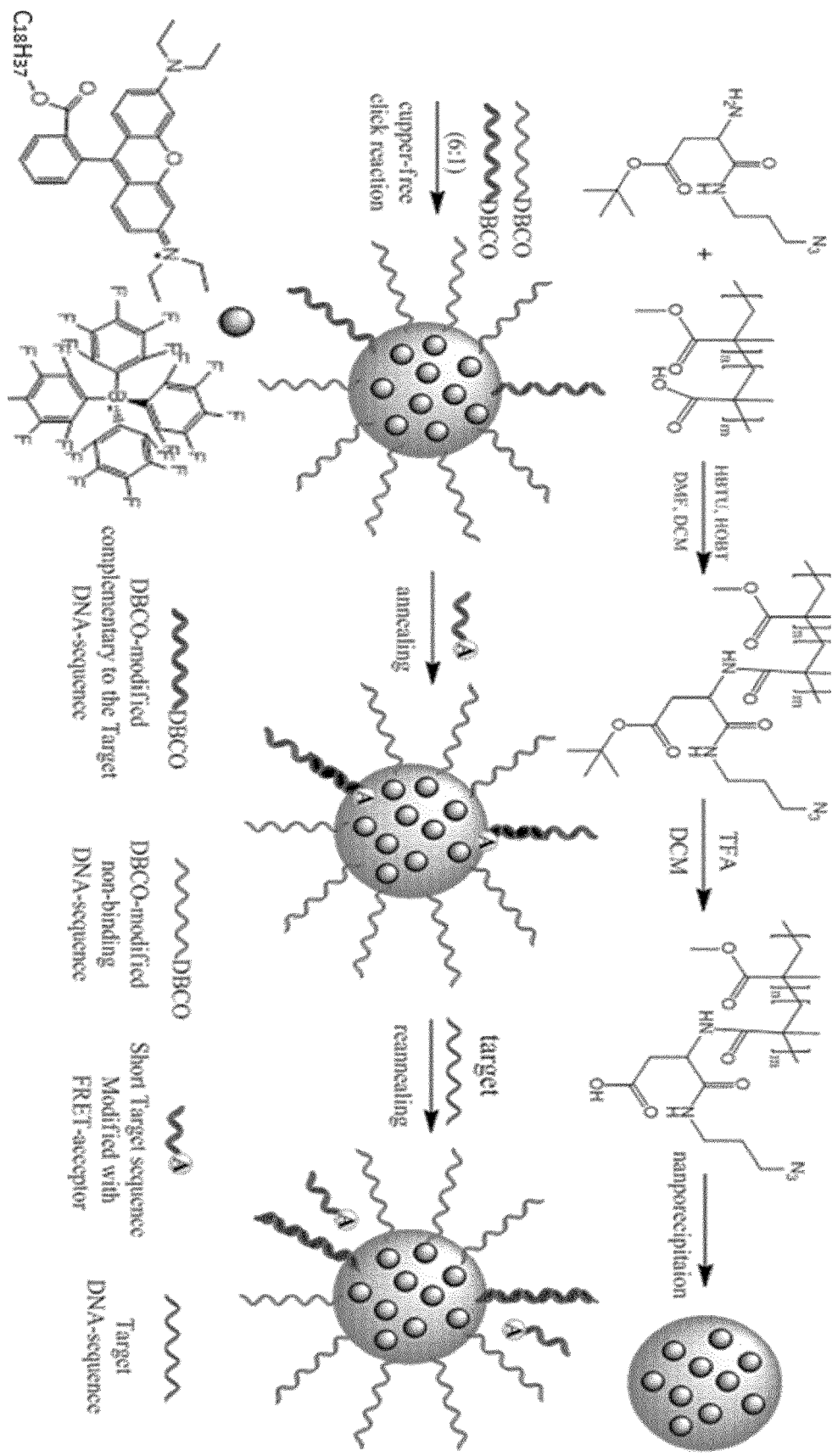

FIG. 2: Scheme of synthesis of oligonucleotide-functionalized nanoparticles of the present invention. It includes (i) conjugation of polymer bearing carboxyl groups and azide groups; (ii) nanoprecipitation of the polymer, (iii) DNA attachment to the surface of dye-loaded NPs, hybridization with acceptor probe, target detection.

FIG. 3: Size of NPs by dynamic light scattering. Polymers used for nanoprecipitation: PMMMA-MA modified with 3-aminopropylazide (designed as control); commercial PMMA-MA; AspN3, Asp2N3 and Asp3N3—PMMA-MA bearing the motif AspN3, Asp2N3 or Asp3N3 (designed as AspN3, Asp2N3, Asp3N3).

Figure 4A:
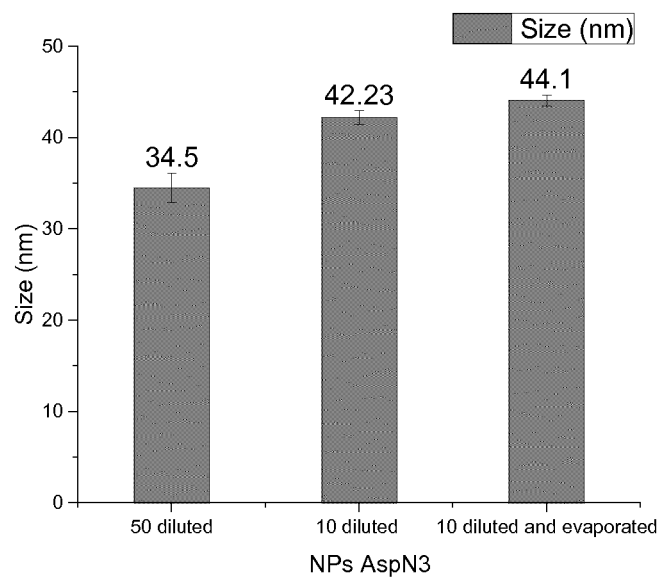
Figure 4B:
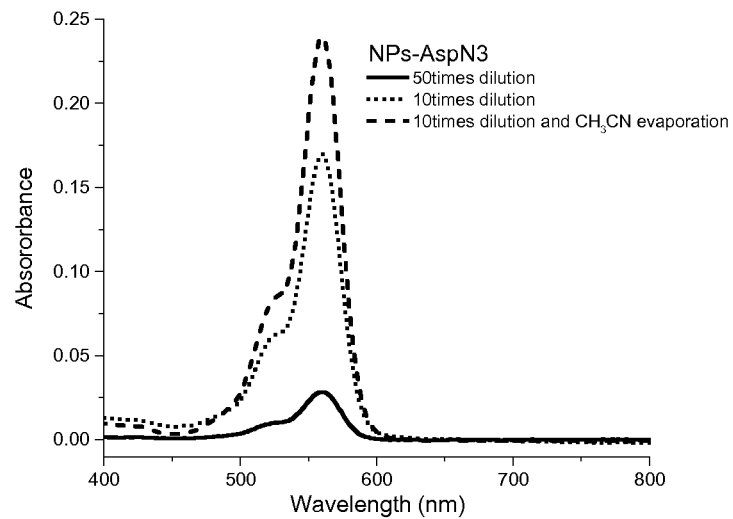

FIGS. 4a and 4b: FIG. 4a shows hydrodynamic diameter of NPs (by DLS) prepared at low and high concentrations. FIG. 4b shows absorption spectra of NPs showing that the new protocol can increase sample concentration manifold.

Figure 5:
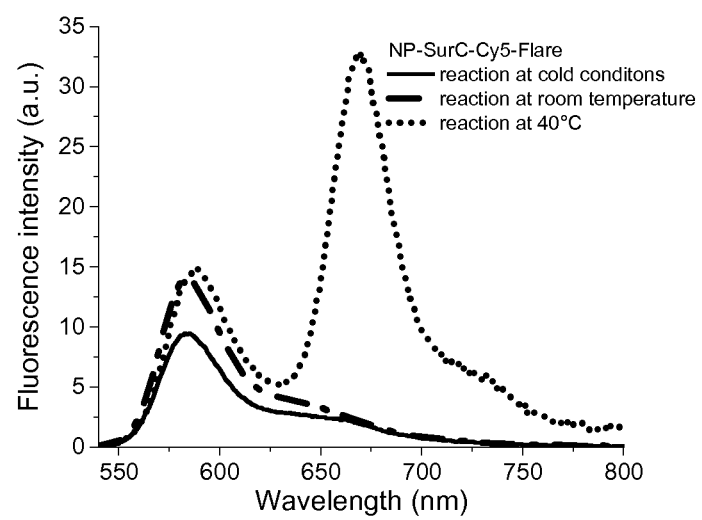

FIG. 5: Fluorescence spectra of NPs at cold condition (line represented by —), room temperature (line represented by •—•—), or 40° C. (line represented by ••••) of conjugation with nucleic acids. To NP-Asp-N3 was added 10 µM of SurC and after 16 h of reaction hybridized with 10 µM of acceptor probe Cy5-Flare. Purification was performed using 20 mM phosphate buffer.

FIGS. 6a-6g show characterization of oligonucleotide-functionalized nanoparticles.

Figure 6A:
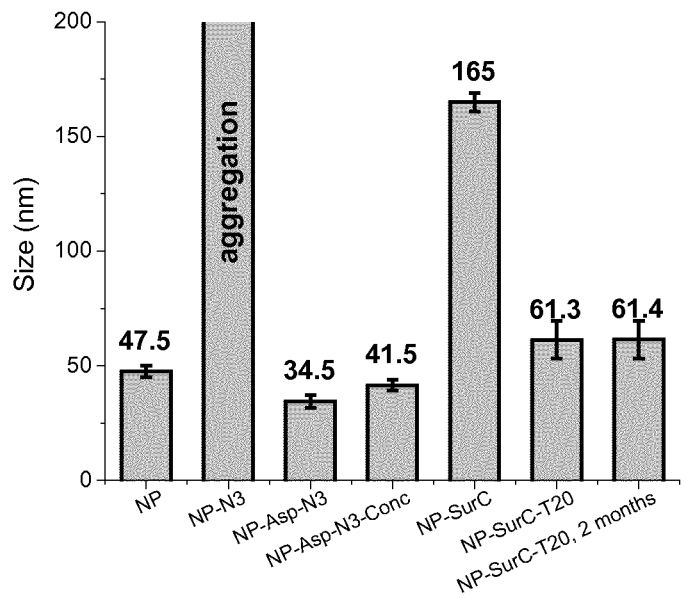

FIG. 6a: Size by DLS of non-modified NPs (NP), NPs only bearing azide groups (NP-$N_3$), NPs bearing the motif Asp-$N_3$ (NP-Asp-$N_3$), NPs bearing Asp-$N_3$ prepared at high concentration (NP-Asp-$N_3$-Conc), NPs bearing the motif Asp-$N_3$ and target-specific oligonucleotide (NP-SurC), NPs bearing the motif Asp-$N_3$, target-specific oligonucleotide and non-specific oligonucleotide (NP-SurC-T20), the latter after 2 months storage (NP-SurC-T20, 2 months).

Figure 6B:
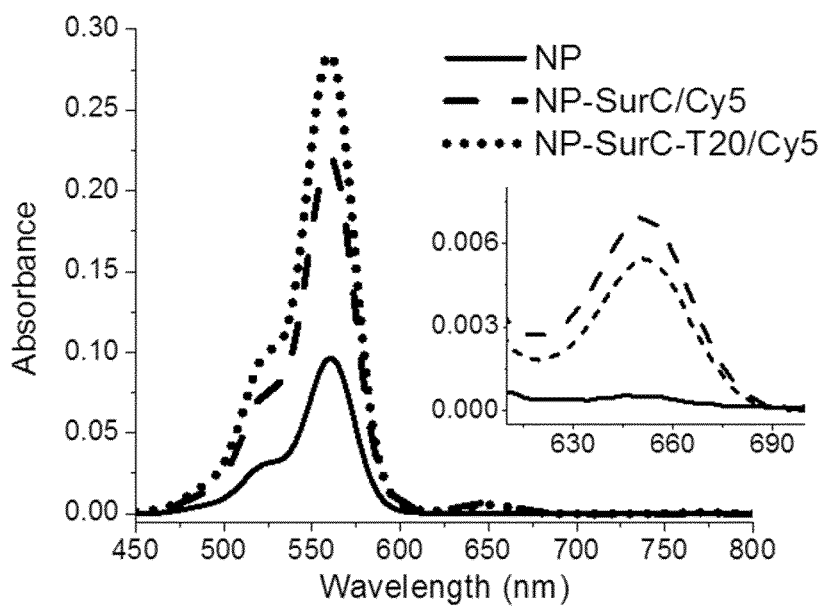

FIG. 6b: Absorption of non-modified NPs (NP), of NPs bearing the motif Asp-$N_3$, target-specific oligonucleotide and acceptor probe Cy5-Flare (NP-SurC/Cy5), of NPs bearing the motif Asp-$N_3$, target-specific oligonucleotide, non-specific oligonucleotide and acceptor probe Cy5-Flare (NP-SurC-T20/Cy5).

Figure 6C:
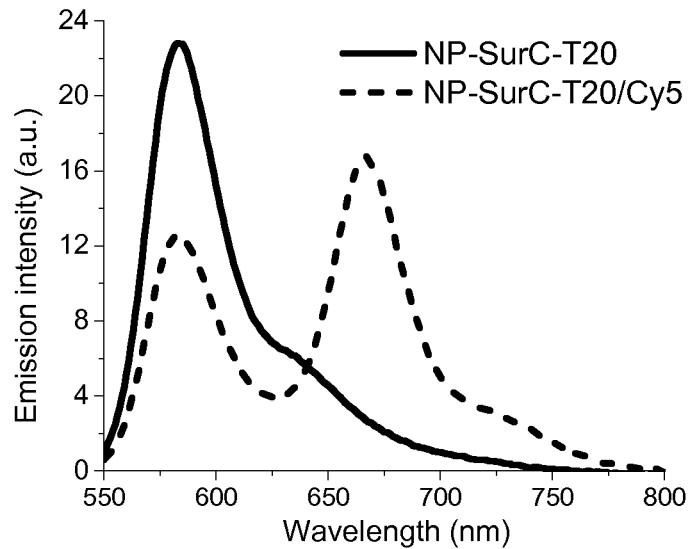

FIG. 6c: fluorescence spectra of NPs bearing the motif Asp-$N_3$, target-specific oligonucleotide and non-specific oligonucleotide (NP-SurC-T20), and of NPs bearing the motif Asp-$N_3$, target-specific oligonucleotide, non-specific oligonucleotide and acceptor probe Cy5-Flare (NP-SurC-T20/Cy5).

Figure 6D:
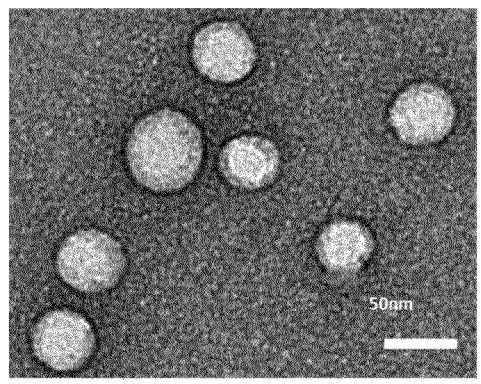
Figure 6E:
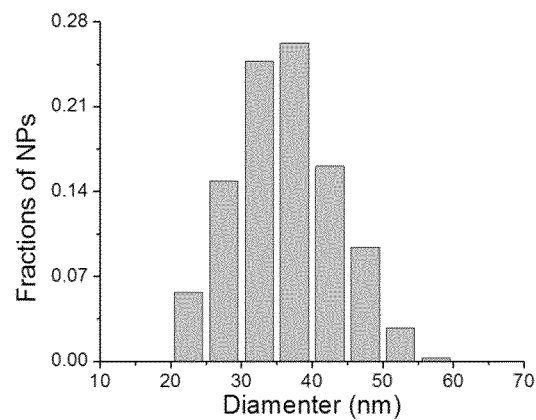

FIGS. 6d and 6e: TEM images of non-modified NPs and corresponding size distribution statistics.

Figure 6F:
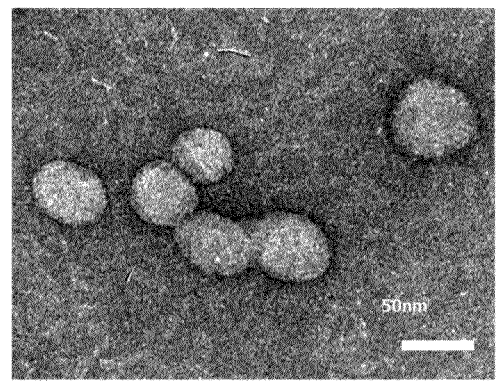
Figure 6G:
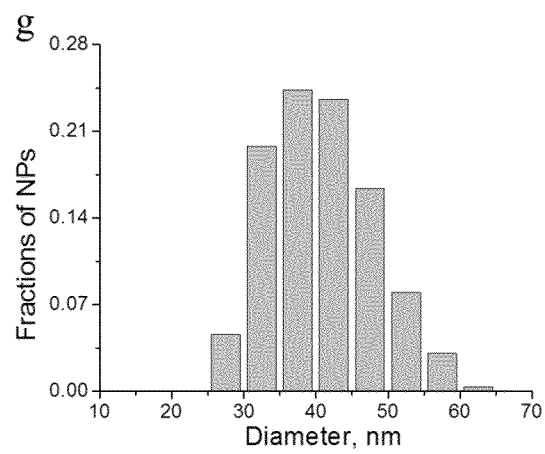

FIGS. 6f and 6g: TEM images of oligonucleotide-functionalized NPs and corresponding size distribution statistics.

Figure 7:
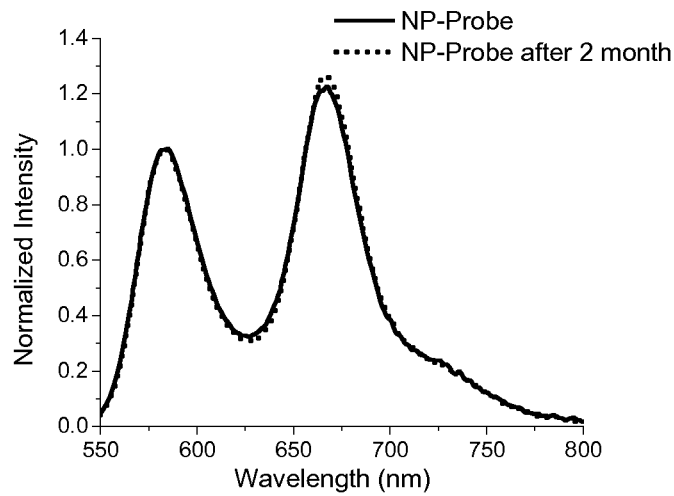

FIG. 7: Fluorescence emission spectra of oligonucleotide-functionalized NPs immediately after preparation and after 2 months storage in the dark at 4° C. The spectra are normalized at the short-wavelength band.

FIGS. 8a-8d show response of oligonucleotide-functionalized NPs to the target.

Figure 8:
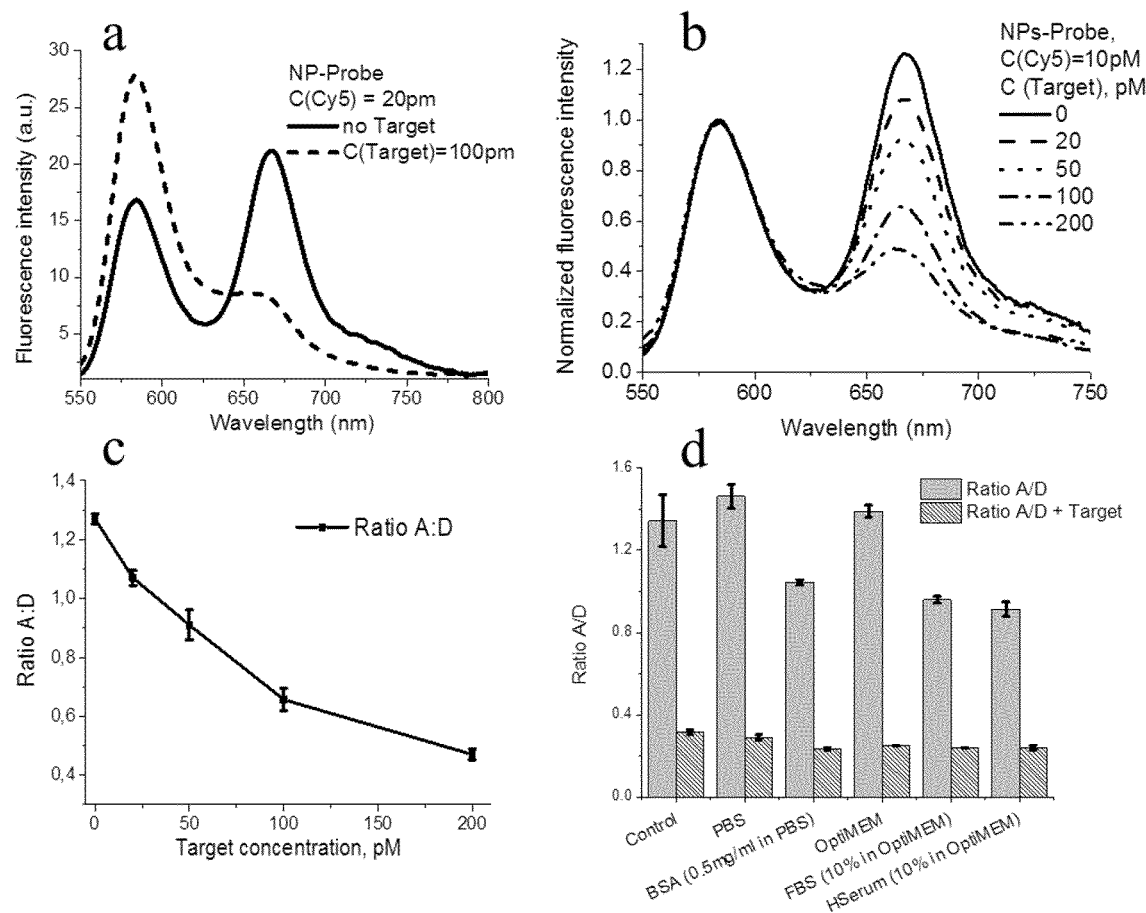

FIG. 8a: Fluorescence spectra of oligonucleotide-functionalized NPs with concentration of Cy5-Flare 20 pM after keeping overnight at 4° C. without Target (Control) and with Target (100 pM).

FIG. 8b: Fluorescence spectra of oligonucleotide-functionalized NPs after incubation with target at different concentrations: 0 (Control), 20, 50, 100 and 200 pM.

FIG. 8c: A/D ratio values of oligonucleotide-functionalized NPs after incubation with target at different concentrations: 0 (Control), 20, 50, 100 and 200 pM.

FIG. 8d: A/D ratio response of the probe (100 pM Cy5-Flare) to the target (500 pM) in different biological media FIGS. 9a-9f: Single-particle imaging of immobilized oligonucleotide-functionalized NPs.

Figure 9A:
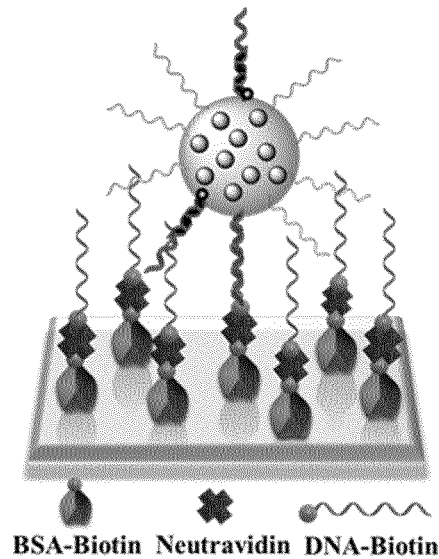

FIG. 9a: The oligonucleotide-functionalized NPs on a BSA-biotin-neutravidin-biotin-A20 surface is shown. The hybridization with surface occurs due to formation of A20-biotin and T20-NP double strand.

Figure 9B:
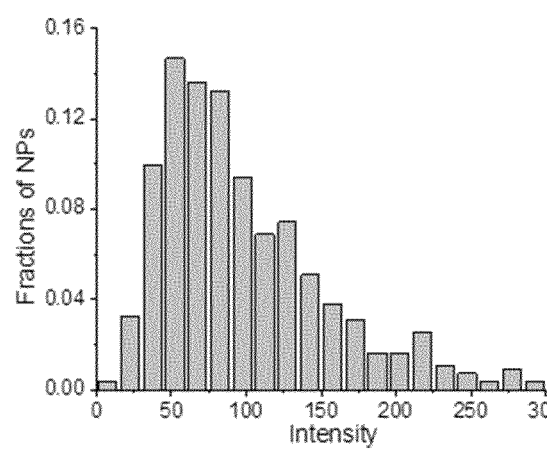

FIG. 9b: Single particle total intensity distribution of donor in NP-T20.

Figure 9C:
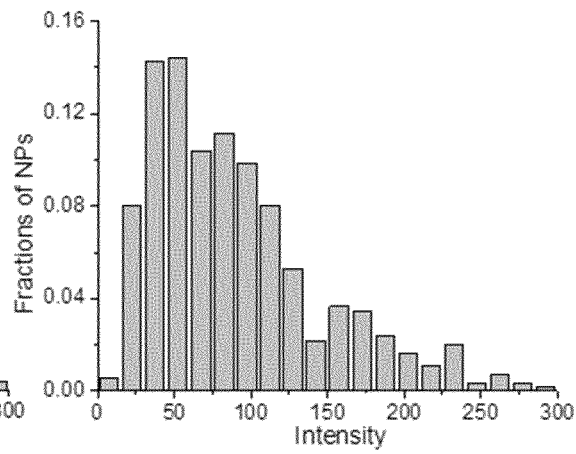

FIG. 9c: Sum of FRET-donor and FRET-acceptor in oligonucleotide-functionalized NPs (nanoprobes).

FIG. 9d: Wild-field microscopy images of the nanoprobes at the acceptor, donor and merged channels (both channels are represented at the same intensity scale). The excitation was at 550 nm with excitation power 0.2 mW at the sample level. Integration time was 200 ms.

FIG. 9e: Direct excitation of the acceptor (650 nm with laser power 10 mW and the integration time 200 ms).

FIG. 9f: Signal amplification (antenna effect) of oligonucleotide-functionalized NPs at the single-particle level presented as a distribution histogram. At least 1500 NPs were analysed.

Figure 10:
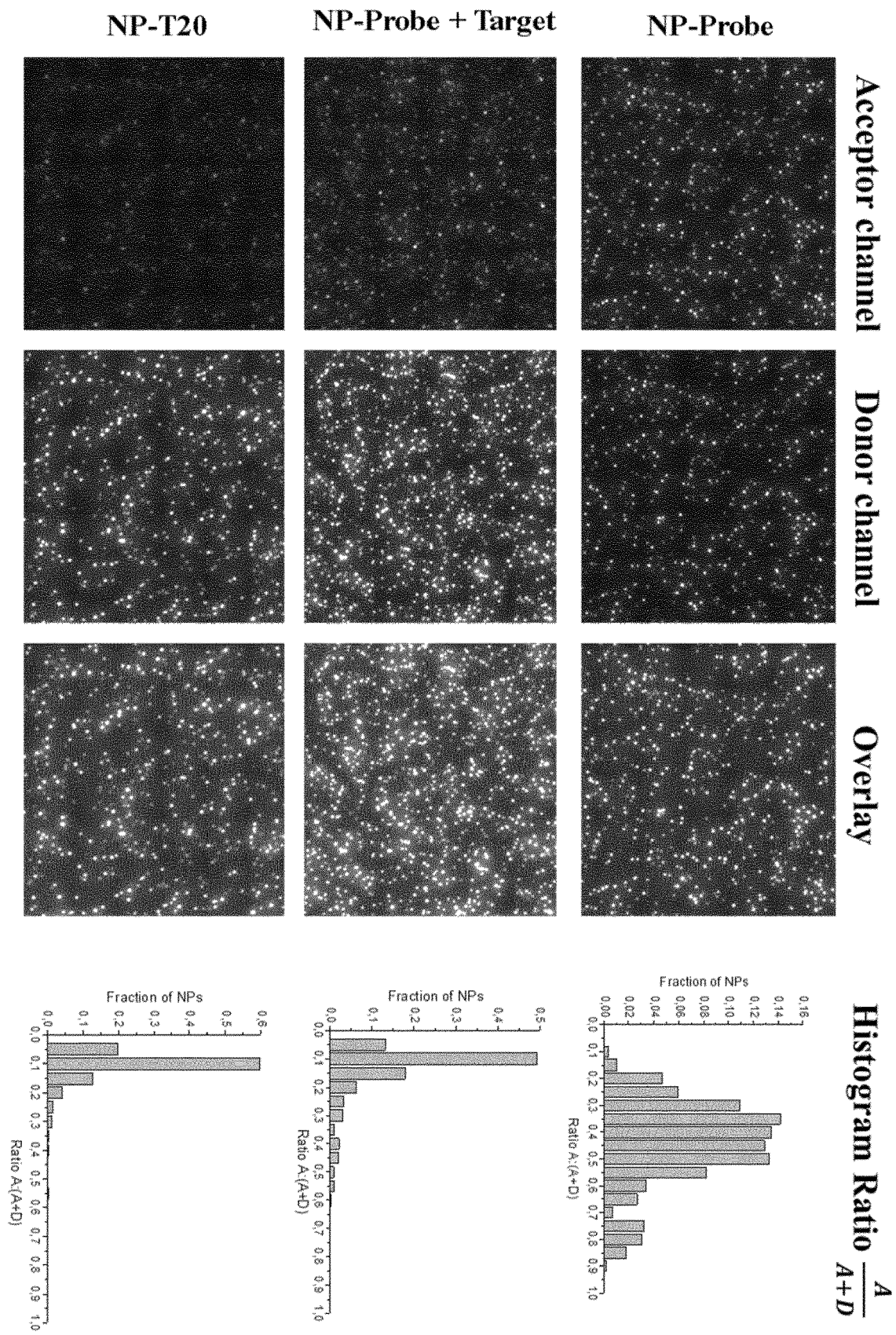

FIG. 10: Response to the target at the single particle level. (a) Wild-field microscopy images using GEMINI setup of the oligonucleotide-functionalized NPs (first row), after target addition and 30 min incubation at room temperature (second row) and control NP-T20 (third row). All channels are represented at the same intensity scale. The excitation was at 550 nm (excitation power was 0.20 mW, integration time was 200 ms). (b) Corresponding distribution histograms of relative FRET for nanoprobe, nanoprobe with target (1 nM) and control NP-T20.

EXAMPLES

1. Materials and Methods

Materials

Chemical compounds: Poly (methyl methacrylate-co-methacrylic acid) (PMMA-MA, 1.6% methacrylic acid, Mn ~15000, Mw ~34000), 3-chloropropanamine hydrochloride (98%), rhodamine B octadecyl ester perchlorate (>98.0%), lithium tetrakis (pentafluorophenyl)borate ethyl etherate, N,N-dimethylformamide (anhydrous, 98%), N,N-Diisopropylethylamine (≥99%), acetonitrile (anhydrous, 99.8%), dichloromethane (anhydrous, ≥99.8%), 1-Hydroxybenzotriazole (≥97%), BSA-biotin, Amicon Centrifugal filters (0.5 mL, 100K) were purchased from Sigma-Aldrich. Citric acid monohydrate (≥99.5%), sodium azide (99%), sodium iodide (≥99.5%) and trifluoroacetic acid (99%) were purchased from Alfa Aesar. Fmoc-Asp(OtBu)—OH was purchased from Activotec. HBTU was purchased from ChemPep Inc. Neutravidin and LabTek chambers (Borosilicate cover glass, eight wells) were purchased from Thermo Scientific. Lyophilized single strand DNA sequences were purchased from IBA, dissolved in Milli-Q water, aliquoted and stored at −20° C. for further experiments.

Sodium phosphate monobasic (>99.0%, Sigma-Aldrich) and sodium phosphate dibasic dihydrate (>99.0%, Sigma-Aldrich) were used to prepare 20 mM phosphate buffers at pH 7.4. For saline buffer sodium chloride (≥99%, Sigma Aldrich) 30 mM and magnesium chloride (≥98%, Sigma Aldrich) 12 mM was added to 20 mM phosphate buffer and pH was adjusted with sodium hydroxide 1N solution. Milli-Q water (Millipore) was used in all experiments. For immobilization protocol DPBS (without $Ca^{2+}$ and $Mg^{2+}$) was purchased from Lonza.

Synthesis of the Linker

Fmoc-Asp-Cl tert-butyl 3-[(3-chloropropyl) carbamoyl]-3-[[(9H-fluoren-9-ylmethoxy)carbonyl]amino] propanoate—Fmoc-Asp(OtBu)—OH (1 eq 6 mmol 2.47 g), HBTU (1.2 eq 7.2 mmol 2.73 g) and HOBt (1.3 eq 7.8 mmol 1.05 g) were dissolved in 30 ml of anhydrous N,N-dimethylformamide. After complete dissolution the N,N-diisopropylethylamine (3 eq 18 mmol 2.97 mL) was added to the stirring mixture under argon at room temperature and in 15 min 3-chloropropanamine hydrochloride (1 eq 6 mmol 0.78 g) was added. The reaction was stirred for 24 h and completion of the reaction was checked by TLC (DCM/MeOH 98/2). The solvent was evaporated under reduced pressure, the residue was diluted with water and precipitate was collected. The crude product was washed with solution of citric acid, followed by solution of sodium bicarbonate. After the crude product was purified by column chromatography (DCM/MeOH 98/2), the product was obtained as pale-yellow solid (2.3 g 80% yield). $^1$H NMR (400 MHz, CDCl$_3$) δ ppm 1.46 (s, 9H), 1.98 (quin, J=6.30 Hz, 2H), 2.60 (dd, J=16.75, 6.24 Hz, 1H), 2.95 (br d, J=15.16 Hz, 1H), 3.45 (m, 2H), 3.56 (br t, J=6.24 Hz, 2H), 4.23 (m, 1H), 4.36-4.60 (m, 3H), 5.93 (br s, 1H), 6.59 (br s, 1H), 7.27-7.36 (m, 2H), 7.42 (t, J=7.50 Hz, 2H), 7.60 (d, J=7.34 Hz, 2H), 7.78 (d, J=7.58 Hz, 2H). $^{13}$C NMR (101 MHz, CDCl$_3$) δ, ppm: 28.00, 31.99, 37.09, 37.43, 42.23, 47.20, 51.19, 67.14, 81.95, 120.06, 120.08, 121.01, 124.98, 125.00, 127.09, 127.12, 127.81, 141.35, 141.38, 143.65, 143.70, 156.10, 170.71, 171.27. HR/LC/MS for $C_{26}H_{31}ClN_2O_5$ m/z (M+) calc 487.19, found 487.19706.

Asp-N$_3$—Fmoc-Asp-C (1 eq 3 mmol 1.5 g), sodium azide (5 eq 15.4 mmol 1 g) and sodium iodide (1 eq 3 mmol 0.47 g) were dissolved in anhydrous N,N-dimethylformamide (20 ml) and stirred under Ar overnight at 60° C. After the solvent was evaporated, the residue was extracted with water/DCM and washed twice with brine. The crude product was purified by column chromatography (DCM/MeOH 94/6). By LCMS and NMR was observed Fmoc deprotected Asp-N3 as pale-yellow oil (460 mg 55% yield). $^1$H NMR (400 MHz, CDCl3) δ ppm: 1.46 (s, 9H), 1.65 (m, 2H), 1.81 (quin, J=6.72 Hz, 2H) 2.57 (dd, J=16.63, 8.07 Hz, 1H) 2.8-2.85 (m, 1H) 3.29-3.44 (m, 4H) 3.63 (dd, J=8.07, 3.67 Hz, 1H), 7.57 (br s, 1H). $^{13}$C NMR (101 MHz, CDCl$_3$) δ ppm 28.08, 28.89, 36.65, 40.52, 49.20, 52.02, 81.15, 171.24, 173.71. HR/LC/MS for $C_{11}H_{21}N_5O_3$ m/z (M+) calc 272.17, found 272.17153.

Polymer

PM-Asp-N3-Boc. The PMMA-MA (1 eq of COOH groups, 0.06 mmol, 400 mg) was dissolved in anhydrous N,N-dimethylformamide (5 ml). To this solution HBTU (3 eq, 0.183 mmol, 70 mg), HOBt (4 eq, 0.24 mmol, 33 mg) and N,N-diisopropylethylamine (10 eq 0.61 mmol 0.1 mL) was added. The mixture was stirred for 15 min and after Asp-N3-Boc (3 eq 0.183 mmol 50 mg) was added. The reaction was stirred overnight at room temperature under argon. The solvent was evaporated under reduced pressure and residue was dissolved in minimum of acetonitrile and precipitate with methanol. The precipitate was washed with methanol, redissolved in acetonitrile and reprecipitated twice in methanol. After drying under a vacuum, product was obtained as a white solid—220 mg, yield 55%. $^1$H NMR (400 MHz, CDCl$_3$) δ, ppm: 0.85 (br s, 2H), 1.02 (br s, 1H), 1.18-1.29 (m, 1H), 1.46 (br s, 1H), 1.65 (br s, 1H), 1.74-2.11 (m, 2H), 3.60 (br s, 3H). (Degree of modification 82% calculated from BOC signal in NMR spectra).

PM-Asp-N$_3$—PM-Asp-N$_3$-Boc (200 mg) was dissolved in anhydrous dichloromethane (5 mL) and 2 mL of trifluoroacetic acid was added. The mixture was stirred vigorously for 3 hours. Then solvents were evaporated under reduced pressure. To the residue the acetonitrile was added and evaporation was repeated several times until the absence of the trifluoroacetic acid. Then the product was precipitated in methanol and filtrated. After drying under a vacuum, the product was obtained as a white solid—160 mg, yield 80%. $^1$H NMR (400 MHz, CDCl$_3$) δ, ppm: 0.78-1.11 (m, 2H), 0.94-1.11 (m, 1H), 1.24 (br s, 1H), 1.45 (br s, 1H), 1.72-2.15 (m, 2H), 3.61 (br s, 3H).

Rhodamine B octadecyl ester trakis(penta-fluorophenyl) borate (R18/F5) was synthesized by ion exchange and purified by column chromatography as described previously. (Reisch, A. et al. Nat. Commun. 5, 4089 (2014))

Nanoparticle Preparation. Stock solution of the polymers in acetonitrile was prepared at a concentration of 1 or 2 mg ml$^{-1}$ containing R18/F5-TPB (30 wt % relative to the polymer). 50 μL of the polymer solutions were then added quickly using a micropipette and under shaking (Thermomixer comfort, Eppendorf, 1100 rpm) to 450 μL of 20 mM phosphate buffer. The particle solution was then quickly diluted 5-fold with the same buffer. For preparation of NPs functionalized with DNA the protocol was slightly different (see below).

NP-Probe synthesis. 100 μL of the polymer solution in acetonitrile (2 mg ml$^{-1}$ with 30 wt % R18/F5-TPB relative to the polymer) were then added quickly using a micropipette and under shaking (Thermomixer comfort, Eppendorf, 1,100 rpm) to 900 μL of 20 mM phosphate buffer, pH7.4 at 21° C. After the residues of acetonitrile was evaporated. Aliquots of DNA were added to 300 μL of nanoparticles. The reaction was mixed and kept overnight at 40° C. on Thermomixer without shaking protected from light. Then the reaction was cooled down to room temperature. For annealing with Flare-Cy5, the aliquot of Flare-Cy5 in ratio 1:1 with SurC was added and mixture was heated for 70° C. in water bath for 3 mins. To complete hybridization the reaction was cooled down to room temperature and kept in the dark for 2 hours. Then the mixture was diluted with 20 mM phosphate buffer containing 12 mM MgCl$_2$ and NaCl 30 mM to 4 mL and purified by centrifugation using centrifuge filters (Amicon, 0.5 ml, 100 k) on 1000 g at 20° C. for 2 min. The procedure of centrifugation was repeated 5 times to remove the non-reacted oligonucleotides. The obtained NP-probes in volume 1 mL were kept in the dark at 4° C.

Nanoparticle characterization. Measurements for the determination of the size of nanoparticles were performed on a Zetasizer Nano ZSP (Malvern Instruments S.A.). The mean value of the diameter of the size distribution per volume was used for analysis. Absorption spectra were recorded on a Cary 4000 scan UV-visible spectrophotometer (Varian), excitation and emission spectra were recorded on a FluoroMax-4 spectrofluorometer (Horiba Jobin Yvon). For standard recording of fluorescence spectra, the excitation wavelength was set to 530 nm. The fluorescence spectra were corrected for detector response and lamp fluctuations. To calculate FRET efficiency based on fluorescence spectra, a classical equation was used: $E_{FRET}=1-I_{D-A}/I_D$, where $I_D$ is the integral donor intensity and $I_{D-A}$ is the integral intensity of the donor in the presence of the acceptor.

Amplification factor of the acceptor emission (antenna effect, AE) was expressed as the ratio of the maximal excitation intensity of the donor to that of the acceptor with correction from the emission of the donor dyes at 690 nm:[14]

$$AE = \frac{I^{ex}_{D-FRET} - I^{ex}_D * \frac{I^{em}_{D-FRET}}{I^{em}_D}}{I^{ex}_{A-FRET} - I^{ex}_A}$$

Where $I_{D-FRET}^{ex}$ and $I_{A-FRET}^{ex}$ are the maximal excitation intensities of donor and acceptor in NP-Probe, respectively;

$I_D^{ex}$ and $I_A^{ex}$ are the excitation intensities at the wavelengths of excitation maximum of donor and acceptor in NP-SurC-T20; $I_{D\text{-}FRET}^{em}$ and $I_D^{em}$ maximum emission intensity of donor for NP-Probe and NP-SurC-T20, respectively.

Quantum yields of donor in NPs were calculated using Rhodamine 101 in methanol as a reference (QY=1.0) with an absorbance of 0.01 at 530 nm. (Karstens, T. & Kobs, K. J. Phys. Chem. 84, 1871-1872 (1980)). QYs of an acceptor were measured using DiD in methanol (QY=0.33) as a reference. (Texier, I. et al. J. Biomd. Opt. 14, 054005 (2009)).

Transmission Electron Microscopy (TEM)

Carbon-coated copper-rhodium electron microscopy grids with a 300 mesh (Euromedex, France) were surface treated with a glow discharge in amylamine atmosphere (0.45 mbar, 4-4.5 mA, 22 s) in an Elmo glow discharge system (Cordouan Technologies, France). Then, 5 µL of the solution of NPs at 0.04 g/L were deposited onto the grids and left for 2 min. The grids were then treated for 1 min with a 2% uranyl acetate solution for staining. They were observed with a Philips CM120 transmission electron microscope equipped with a LaB6 filament and operating at 100 kV. Areas covered with nanoparticles of interest were recorded at different magnifications on a Peltier cooled CCD camera (Model 794, Gatan, Pleasanton, Calif.). Image analysis was performed using the Fiji software.

Fluorescence Microscopy.

Immobilization of nanoparticles in LabTek chamber was performed according to Protocol (Jurgen J Schmied et al, Nature Protocols, Vol. 9, NO 6, 2014): The LabTek chamber was washed 3 times with DPBS followed by incubation with 200 µl of BSA-Biotin (0.5 mg ml$^{-1}$ in DBPS) for 5 min. Then BSA-biotin solution was removed and the chamber was washed 3 times with 500 µl of DPBS. After the chamber was incubated with 200 µL of neutravidin solution (0.5 mg ml$^{-1}$ in DBPS) for 5 min and washed 3 times with 500 µL of DPBS. Then the camber was incubated with 200 µL of 1 µM solution of A20-biotin in DPBS for 5 min and washed 3 times with 20 mM phosphate buffer containing 12 mM MgCl$_2$ and NaCl 30 mM. Then NP-Probe solution was deposed with proper concentration to achieve desired density and incubated for 1 hour at room temperature in the dark. Before measurements the chamber was washed 2 times with 20 mM phosphate buffer containing 12 mM MgCl$_2$ and NaCl 30 mM and covered with 200 µL of the same buffer.

Single particle measurements were performed in the epi-fluorescence mode using Nikon Ti-E inverted microscope with an objective (Apo TIRF 100X, oil, NA 1.49, Nikon). A 550 nm a 650 nm light emitting diodes were used to excite the samples. The 550 nm light power was set to 0.2 mW. For direct excitation of acceptor Cy5, the 650 nm light was used with a power of 10 mW. The fluorescence signal was recorded with a Hamamatsu Orca Flash 4 camera. The exposure time was set to 200 ms per image frame. To enable two color images W-VIEW GEMINI image splitting optics were used with the following filter set: dichroic 640 nm (Semrock FF640-FDi01-25×36), were used to image R18/F5-TPB and Cy5, respectively. Single particle analysis was performed using the Fiji software: particle locations were detected through a Fiji routine applied to a projection (maximum intensity) of 3 frames. After the automatic background subtraction, the mean intensities of circular regions of interest with a diameter of 8 pixels around the found particle locations were then measured. At least three image sequences (245 pixel×245 pixel) per condition were analyzed with, on average, 500-700 particles per sample. The amplification factor of acceptor emission at a single particle level was determined using:

$$AF = \frac{I_A^{550 nm}}{I_A^{650 nm}} \times \frac{P^{650 nm}}{P^{550 nm}}$$

Where $I_A^{550\ nm}$ and $I_A^{650\ nm}$ are mean intensities of acceptors under excitation at 550 and 650 nm, respectively, and $P^{650\ nm}$ and $P^{550\ nm}$ are laser powers corresponding wavelength.

2. Experimental Results 2.1 NPs Synthesis and DNA Modification

Nanoparticles were obtained by nanoprecipitation. In case of control polymer bearing azide group without carboxyl group, large aggregates were formed (FIG. 3). By contrast, polymers bearing the motif AspN3 can produce the particles with the size of 32-36 nm. Remarkably, with the increase of number of carboxyl groups on the surface the size of NPs was decreasing.

For the effective reaction between DNA and the dye-loaded NPs, it's necessary to achieve micromolar concentrations of the NPs functional groups. The increase of azide concentration can be calculated by the increase of dye donor encapsulated in the NPs, since dye donor content is about 30 wt. % of that of polymer. Common protocol of nanoprecipitation usually includes 50 times dilution from initial stock solution of polymer (1 g/L) with the dye in CH$_3$CN. This procedure allows obtaining 30-40 nm NPs with total concentration of reactive azide groups at 0.6-1.3 µM. To increase the concentration of functional groups, the protocol of nanoprecipitation is modified. First, the concentration of the polymer in acetonitrile is increased to (2 mg/ml), while keeping dye content at 30 wt. % with respect to polymer. Then, 100 µl of this acetonitrile stock solution was added to phosphate buffer (900 µL), followed by evaporation of the acetonitrile from the mixture. DLS data suggests that the size of NPs only slightly increased for NPs obtained by the new method and evaporation of acetonitrile did not influence significantly the particle size. Moreover, according to absorption spectroscopy, new protocol allowed increasing the concentration of dye-loaded NPs around 9-fold (FIG. 4).

For the attachment of DNA to NPs cupper-free click reaction is carried out between DNA modified with DBCO and NPs containing azide groups on the surface. As DNA sequence, 20 mer encoding survivin (SurC), which is an important cancer marker, is used. The reaction of the concentrated NPs and Sur-C was realized at 4, 20 and 40° C. for 18 h. To monitor the reaction, the reaction mixture was annealed with complementary Flare-Cy5, which is shorter strand (12NA) labelled with Cy5 (FRET acceptor). NPs were loaded with RhC18-F5 (FRET-donor). The excess of DNA was removed by repeating (5 times) filtration through 100 kDa filters. The efficiency of purification was monitored by absorbance. Fluorescence spectra revealed that at 4 and 20° C. the reaction is not occurred, while at 40° C. it was observed a clear FRET signal from particle to hybridized DNA, indicating successful conjugation reaction (FIG. 5). The evidence for grafting was also provided by absorption spectroscopy: absorption of the acceptor-flare was clearly observed in the purified samples, in contrast to negative control, where NPs without azide group were mixed with Sur DNA. However, in PBS buffer containing 12 mM Mg$^{2+}$ ions (required for formation of stable duplexes), NPs-DNA conjugates showed relatively large size (FIG. 6a), probably because of partial aggregation of the obtained NPs in high-salt conditions.

2.2 Optimization of Sensor and Characterisation of NPs with DNA

To achieve the highest optical amplification through a light-harvesting mechanism, it need to ensure high donor/acceptor ratio in the nanoprobe of the invention. This means that the minimal amount of DNA/acceptor-flare should be grafted to the particle surface, but the number of grafted acceptors should be large enough to ensure efficient FRET. On the other hand, large number of nucleic acids should improve colloidal stability of NPs in biological media, which is supported by a recent report for NPs built from ring-opening metathesis block copolymers.[13] Therefore, to ensure controlled small amount of coding nucleic acids and particle stability, the reaction of NPs with a mixture of coding (SurC) and non-coding DNA (T20) was performed. Addition of T20 (20 µM) to the SurC (3 µM) did not inhibit the grafting of SurC to NPs surface, as evinced by absorption spectroscopy (FIG. 6b). Indeed, in comparison to NPs reacted with SurC (3 µM) without T20, only a slight decrease in the absorbance of acceptor-Flare was observed. Fluorescence spectra showed strong emission of the FRET acceptor hybridized on SurC for both type of samples (see FIG. 6 for NPs modified with SurC and T20), which confirmed successful grafting of SurC to NPs in both cases. Remarkably, particles containing T20 remained small in high-salt buffer (PBS) with $Mg^{2+}$ ions and there size did not change even after 2 month incubation in this medium (FIG. 6a). Moreover, the emission spectrum of this NP-DNA conjugate, showing both FRET donor and acceptor bands, remained practically invariant for this 2 month period (FIG. 7). These results suggest that excess of non-coding DNA is essential to provide stability to the polymer NPs. Electron microscopy also confirmed that conjugation with nucleic acids preserved the spherical shape and monodispercity of NPs, while their size increased only by ca 5 nm.

The further studies were focused on SurC/T20 NPs, exhibiting most promising properties. The synthesis of these NPs was repeated four times showing good reproducibility of their size and spectroscopic properties (Table 1). Based on absorption data and the particle size from TEM we could estimate that 23±3 (s.e.m. n=4) acceptor-flare units were grafted per particle containing 3200±400 donor dyes. Remarkably, FRET efficiency in this system was 60±6%, indicating that 138±20 donor dyes inside nanoparticle transfer 60% of their energy to a single acceptor located at the NPs surface. This is highly efficient light-harvesting phenomena, which should result in the amplification of the acceptor emission (antenna effect). The antenna effect can be directly measured as a ratio of the donor to acceptor excitation intensity obtained from the excitation spectra recorded at the emission wavelength of the acceptor.[15] The obtained antenna effect was 58±1 with remarkably high reproducibility for all four preparations (Table 1), showing that excitation though NP donor (nano-antenna) amplifies acceptor emission 58-fold. This large signal amplification phenomenon should be of key importance for the next step on detection of the target nucleic acids.

TABLE 1

Size, composition and light-harvesting properties of the NPs-DNA conjugate prepared four times.[a]

| Sample | Size d. nm, by DLS[c] | Ratio D/A | A per NP | FRET efficiency, % | AE |
| --- | --- | --- | --- | --- | --- |
| 1 | 71.8 ± 2.5 | 143.54 | 20.1 | 42.31 | 58.23 |
| 2 | 60.2 ± 2.3 | 116.87 | 25.7 | 66.85 | 56.7 |
| 3 | 61.4 ± 3.1 | 189.64 | 15.8 | 65.08 | 58.19 |
| 4 | 52 ± 1.3 | 101.3 | 29.6 | 66.75 | 57.28 |
| Average[b] | 61 ± 4 | 138 ± 20 | 23 ± 3 | 60 ± 6 | 58 ± 1 |

[a]Statistics by volume was used in DLS data; Ratio D/A is the donor acceptor ratio; A per NP is the number of acceptors per particle; AE is antenna effect.
[b]Avarage values values are shown together with standard error of the mean.
[c]Despite variations in the DLS data, the average size by TEM was relatively stable (40 ± 10 nm), where the error is the full width at half maximum of the size distribution (number of particles analysed >500).

2.3 Detection of Target Nucleic Acids

As a target, a DNA sequence (20 NA) corresponding to a part of survivin gene was used. First, the target at 100 pM concentration was mixed with nanoprobe bearing 20 pM flare (Cy5) (corresponds to 0.87 pM nanoprobe concentration) and incubated at 4° C. for 24 h. It was found that in the presence of the excess of the target DNA, nanoprobe totally lost FRET signal, in contrast the control sample without the target (FIG. 8a). This result shows that, as expected, the target sequence replaced flare-Cy5 at NPs surface, thus stopping FRET. To make an estimation of the limit of detection, NPs were further diluted to flare concentration of 10 pM and added increasing concentrations of the target. Remarkably, the relative intensity of the acceptor gradually decreased (FIG. 8b,c), indicating that the nanoprobe operates well in the studied concentration range (0-200 pM). Based on the obtained concentration dependence the estimated LOD was 5 pM. This remarkably low LOD was achieved for a standard fluorometer and it can be much lower when a dedicated detection setup is used. Then, the nanoprobe was verified whether it is operational in different biological media. In all studied media, namely phosphate buffered saline (PBS), PBS with bovine serum albumin, Opti-MEM (cell culture medium without serum) and DMEM with serum (full cell medium), the probe showed strong ratiometric response to the target: decrease in the FRET signal in the presence of the target. This is a very important result, because it shows that the probe is compatible with highly complex media containing variety of biomolecules, including proteins. Moreover, the nanoprobe of the invention detected successfully the target also in the extract of RNA from cells, showing that it is highly specific to unique nucleic acid sequence in the presence of large variety of other sequences.

2.4 Evaluation of Nanoprobe at the Single-Particle Level

The ultimate test for the performance of the nanoprobe is to verify whether it can operate at the level of single particle. To this end the glass surface was modified with A20 sequence, which are complementary to that of non-coding sequence of the nanoprobe of the present invention. Then, addition of the nanoprobe at 100 pM of Cy5-flare concentration resulted in sufficiently good coverage of the surface. One should notice remarkable homogeneity of the total fluorescence intensity the nanoprobes of the invention at the glass surface, suggesting that the deposition was done successfully without any probe aggregation (FIG. 9c). To evaluate FRET signal at the single particle level, the images of NPs were recorded simultaneously at the green (donor) and acceptor (red) channels. It can be seen in the overlay that the NP-probe showed similar intensities at the donor and acceptor channels as most of NPs appear in yellow. By contrast, control NPs bearing only T20 (NP-T20) showed signal only in the donor channel. These results provide clear evidence that, after immobilization of the surface, the NP-probe of the invention preserved strong FRET, as it was observed in the spectroscopy measurements. Then, to evaluate antenna effect at the single-particle level, emission of the acceptor excited to the nanoprobe (at 550 nm) was compared with its direct excitation at 640 nm. Remarkably, 50-fold higher excitation power density at 640 nm was required to achieve emission intensity comparable to that excited at 550 nm. Quantitative image analysis revealed that the amplification of the acceptor emission thorough the NP-probe of the invention is 75±25. This result is in line with the antenna effect measured using excitation spectra in the cuvette. It is to be noted that, this is the first report, where this high amplification is reported at the single particle level or a biosensor. Previous report that used QD as a FRET donor did not exploit antenna effect because large number of acceptors (~50) should absorb light at least as good as a single QD. The only report on the amplification at the single particle level was reported very recently for a plasmonic biosensor using DNA origami, where the average amplification was 7.3.[10]

Finally, the response of the nanoprobe of the invention to the target at the single particle level was tested (FIG. 10). Immobilized NPs were incubated with excess of the target (1 nM) for 30 min, followed by their two-colour detection. It is clear that after incubation with the target the emission in the red channel strongly decreases, as it was previously observed by fluorescence spectroscopy in the cuvette. The relative FRET efficiency, expressed as A/(A+D), decreased from 0.4 down to 0.1 (FIG. 10), reaching values close to that for the control NPs without FRET acceptor (NP-T20). These results constitute a clear demonstration that the nanoprobe of the invention can report on the presence of target nucleic acids at the single particle level. This implies that ~23 hybridization events at the surface of the nanoprobe (corresponding to the number of flares per NPs) resulted in the color switch of a nano-emitter exhibiting the brightness of >3000 rhodamine dyes. This unique phenomenon has two importance consequences. Firsts, this nearly 6-fold change in the intensity ratio at the two emission channels for ~23 hybridization events implies that, at the single particle level, the nanoprobe could readily detect just a few copies of the nucleic acid target. Moreover, due to the signal amplification produced by light harvesting from >3000 fluorescent dyes, the target nucleic acids could be detected at very low illumination power (~1 W/cm$^2$) of LED in an epi-fluorescence mode, which is ~100 fold-lower that required in the single-molecule detection measurements. The use of low power significantly decreases the background noise and makes it possible detection of a few copies of DNA using relatively weak and inexpensive light sources and relatively simple imaging setup.

REFERENCES

1. He, L.; Lu, D. Q.; Liang, H.; Xie, S. T.; Luo, C.; Hu, M. M.; Xu, L. J.; Zhang, X. B.; Tan, W. H.: Fluorescence Resonance Energy Transfer-Based DNA Tetrahedron Nanotweezer for Highly Reliable Detection of Tumor-Related mRNA in Living Cells. ACS Nano 2017, 11, 4060-4066.

2. Nolan, T.; Hands, R. E.; Bustin, S. A.: Quantification of mRNA using real-time RT-PCR. Nature Protocols 2006, 1, 1559-1582.

3. Ali, M. M.; Li, F.; Zhang, Z.; Zhang, K.; Kang, D.-K.; Ankrum, J. A.; Le, X. C.; Zhao, W.: Rolling circle amplification: a versatile tool for chemical biology, materials science and medicine. Chem. Soc. Rev. 2014, 43, 3324-3341.

4. Dirks, R. M.; Pierce, N. A.: Triggered amplification by hybridization chain reaction. Proc. Natl. Acad. Sci. U.S.A 2004, 101, 15275-15278.

5. Wu, W. B.; Bazan, G. C.; Liu, B.: Conjugated-Polymer-Amplified Sensing, Imaging, and Therapy. Chem 2017, 2, 760-790.

6. Wang, S.; Gaylord, B. S.; Bazan, G. C.: Fluorescein provides a resonance gate for FRET from conjugated polymers to DNA intercalated dyes. Journal of the American Chemical Society 2004, 126, 5446-5451.

7. Chinen, A. B.; Guan, C. M.; Ferrer, J. R.; Barnaby, S. N.; Merkel, T. J.; Mirkin, C. A.: Nanoparticle Probes for the Detection of Cancer Biomarkers, Cells, and Tissues by Fluorescence. Chemical Reviews 2015, 115, 10530-10574.

8. Zhang, C. Y.; Yeh, H. C.; Kuroki, M. T.; Wang, T. H.: Single-quantum-dot-based DNA nanosensor. Nat. Mater. 2005, 4, 826-831.

9. Prigodich, A. E.; Randeria, P. S.; Briley, W. E.; Kim, N. J.; Daniel, W. L.; Giljohann, D. A.; Mirkin, C. A.: Multiplexed Nanoflares: mRNA Detection in Live Cells. Analytical Chemistry 2012, 84, 2062-2066.

10. Ochmann, S. E.; Vietz, C.; Trofymchuk, K.; Acuna, G. P.; Lalkens, B.; Tinnefeld, P.: Optical Nanoantenna for Single Molecule-Based Detection of Zika Virus Nucleic Acids without Molecular Multiplication. Analytical Chemistry 2017, 89, 13000-13007.

11. Reisch, A.; Klymchenko, A. S.: Fluorescent Polymer Nanoparticles Based on Dyes: Seeking Brighter Tools for Bioimaging. Small 2016, 12, 1968-1992

12. Trofymchuk, K.; Reisch, A.; Didier, P.; Fras, F.; Gilliot, P.; Mely, Y.; Klymchenko, A. S.: Giant light-harvesting nanoantenna for single-molecule detection in ambient light. Nature Photonics 2017, 11, 657-+.

13. Banga, R. J.; Krovi, S. A.; Narayan, S. P.; Sprangers, A. J.; Liu, G. L.; Mirkin, C. A.; Nguyen, S. T.: Drug-Loaded Polymeric Spherical Nucleic Acids: Enhancing Colloidal Stability and Cellular Uptake of Polymeric Nanoparticles through DNA Surface-Functionalization. Biomacromolecules 2017, 18, 483-489.

14. Farokhzad, O. C.; Cheng, J. J.; Teply, B. A.; Sherifi, I.; Jon, S.; Kantoff, P. W.; Richie, J. P.; Langer, R.: Targeted nanoparticle-aptamer bioconjugates for cancer chemotherapy in vivo. Proc. Natl. Acad. Sci. U.S.A 2006, 103, 6315-6320.

15. Reisch A, Runser A, Arntz Y, Mély Y, Klymchenko A S. Charge-controlled nanoprecipitation as a modular approach to ultrasmall polymer nanocarriers: making bright and stable nanoparticles. ACS Nano 2015, 9, 5104.

16. Woller, J. G.; Hannestad, J. K.; Albinsson, B.: Self-Assembled Nanoscale DNA-Porphyrin Complex for Artificial Light Harvesting. Journal of the American Chemical Society 2013, 135, 2759-2768

The invention claimed is:

1. A dye-loaded polymeric nanoparticle comprising:
a hydrophobic polymer chain, said chains bearing at least one moiety of formula (I),

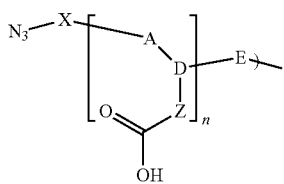

Formula (I)

wherein:
A represents a spacer chosen from: —(CH$_2$)$_m$—, —(CH$_2$)$_p$NH—CO(CH$_2$)$_q$—, —(CH$_2$)$_p$CO—NH(CH$_2$)$_q$—, —(CH$_2$)$_p$O(CH$_2$)$_q$—, —(CH$_2$)$_p$NH(CH$_2$)$_q$O—, —(CH$_2$)$_m$CO—, —CO(CH$_2$)$_m$—, each of m, p and q represent independently from each other an integer chosen from 0 to 8, preferably an integer chosen from 0 to 5, more preferably an integer chosen from 0 to 3,
D represents a group chosen from:

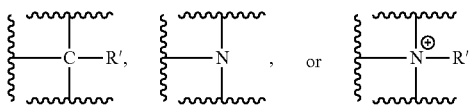

wherein R' represents a hydrogen, a halogen, a (C1-C8)alkyl,
a cyclo(C3-C7)alkyl eventually monosubstituted, a monocyclic non-aromatic heterocyclic group eventually monosubstituted, or a monocyclic aromatic group eventually monosubstituted,
E represents —(Y—NR$_a$—), where R$_a$ is H or an (C1-C8) alkyl,
X, Y, Z are identical or different and each represent independently of the other a spacer chosen from —(CH$_2$)$_r$—, —(CH$_2$—CH$_2$—O)$_r$—, —(CH$_2$—CH$_2$—NH)$_r$—, —(CH$_2$)$_s$NH—CO(CH$_2$)$_t$—, —(CH$_2$)$_s$CO—NH(CH$_2$)$_t$—, wherein r, s and t represent independently from each other an integer chosen from 0 to 8, preferably an integer chosen from 0 to 3,
n represents an integer chosen from 1 to 10, in particular 1 to 3 and wherein at least one of m, p, q, r, s and t have a value different from 0,
when D represents

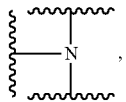 [SMILES: *N(*)*]

E can be absent;
said moiety of formula (I) being bound to a carboxyl group of the polymer and being situated on the surface of the nanoparticle and
energy donors formed by a salt of at least one donor dye and bulky fluorinated anion, said energy donors being encapsulated in the hydrophobic polymer.

2. The dye-loaded polymeric nanoparticle according to claim 1, wherein the chain of the hydrophobic polymer bears at least a moiety of formula (Ia):

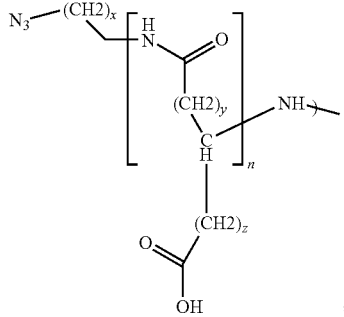

wherein x, y and z represent each an integer chosen from 0 to 8, preferably an integer chosen from 0 to 5, more preferably an integer chosen from 0 to 3.

3. The dye-loaded polymeric nanoparticle according to claim 1, wherein said hydrophobic polymer chain is chosen from polymethacrylates, aliphatic polyesters and polystyrenes, or derivatives thereof.

4. The dye-loaded polymeric nanoparticle according to claim 1, wherein the donor dye is chosen from a rhodamine derivative or a cyanine derivative.

* * * * *